United States Patent [19]
Greenland et al.

[11] Patent Number: 6,037,524
[45] Date of Patent: Mar. 14, 2000

[54] S-ADENOSYL-L-HOMOCYSTEIN HYDROLASE PROMOTER

[75] Inventors: Andrew James Greenland, Bracknell; John Draper, Leicester; Mark Skipsey, Leicester; Simon Warner, Leicester, all of United Kingdom

[73] Assignee: Zeneca Limited, London, United Kingdom

[21] Appl. No.: 08/930,894

[22] PCT Filed: Apr. 10, 1996

[86] PCT No.: PCT/GB96/00882

§ 371 Date: Oct. 9, 1997

§ 102(e) Date: Oct. 9, 1997

[87] PCT Pub. No.: WO96/32488

PCT Pub. Date: Oct. 17, 1996

[30] Foreign Application Priority Data

Apr. 10, 1995 [GB] United Kingdom .................. 9507381

[51] Int. Cl.$^7$ ............................ C12N 15/29; C12N 15/82; C12N 15/84; A01H 5/00
[52] U.S. Cl. ......................... 800/287; 800/279; 800/288; 800/294; 800/298; 800/306; 800/317.2; 800/317.3; 800/317.4; 800/320.1; 800/320.3; 435/411; 435/412; 435/414; 435/417; 435/418; 435/419; 435/421; 435/468; 435/469; 435/320.1; 536/23.6; 536/24.1
[58] Field of Search ............................. 435/172.3, 320.1, 435/419, 418, 411, 412, 414, 417, 421, 468, 469; 536/24.1, 23.6; 800/205, 279, 298, 287, 288, 294, 306, 317.2, 317.3, 317.4, 320.1, 320.3

[56] References Cited

FOREIGN PATENT DOCUMENTS

| 039225 | 10/1990 | European Pat. Off. . |
| 492 536 A2 | 7/1992 | European Pat. Off. . |
| 93/19188 | 9/1993 | WIPO . |

OTHER PUBLICATIONS

Merta et al. The gene and pseudogenes of rat S–adenosyl–L–homocysteine hydrolase. European Journal of Biochemistry. 229:575–582, Apr. 1995.
Schroder et al. cDNA for S–adenosyl–L–homocysteine hydrolase from *Catharanthus roseus*. Plant Physiology. 104:1099–1100, 1994.
Database WPI; Section Ch, Week 9243; Derwent Publications ltd., London, GB; Class C06, AN 92–354683 XP00201269 & JP, A, 04 258 292 (Japan Tobacco Inc), Sep. 14, 1992.
Cantoni et al; The Formation of S–Adenosylho–Mocysteine in Enzymatic Transmethylation Reactions; vol. 76, p. 4744.
Jefferson et al; GUS fusions β–glucuronidase as a sensitive and versatile gene fusion maker in higher plants The EMBO Journal vol. 6, pp. 3901–3907 (1987).
OW et al; Transient and Stable Expression of the Firefly Luciferase Gene in Plant Cells and Transgenic Plants; Science Reports, Nov. 14, 1986, vol. 234; pp. 856–859.

Warner et al.; The Development Expression of the Asparagus Intracellular PR Protein (AoPR1) Gene Correlates With Sites of Phenylpro–Panoid Biosynthesis; The Plant Journal, pp. 31–43, (1994).
Paul et al.; Dedifferentiation of Asparagus Officinalis L. Mesophyll Cells During Intiation of Cell Cultures; Plant Science, 65 pp. 111–117 (1989).
Harikrishna et al.; Wound Response in Mechanically Isolated Asparagus Mesophyll Cells: A Model Monocotyledon System; Journal of Experimental Botany, vol. 42, pp. 791–799, Jun. 1991.
Sganga et al.; Mutational and Nucleotide Sequence Analysis of S–Adenosyl–L–Homocysteine Hydrolase From *Rhodobacter capsulatus*; Proc. Natl. Acad. Sci. USA; vol. 89, pp. 6328–6332, Jul. 1992.
Kawalleck et al.; Induction by Fungal Elicitor of S–Adenosyl–L–Methionine Synthetase and S–Adenosyl–L–Homocysteine Hydrolase mRNAs in Cultured Cells and Leaves of *Petroselinum crispum*; Natl. Acad. Sci, USA; vol. 89, pp. 4713–4717, May 1992.
Kasir et al.; Amino Acid Sequence of S–Adenosyl–L–Homocysteine Hydrolase From *Dictyostelium Discoideum* as Deduced From the Cdna Sequence; Biochemical and Biophysical Research Communications, vol. 153, pp. 359–364, (1988).
Ogawa et al.; Amino Acid Sequence of S–Adenosyl–L–Homocysteine Hydrolase From Rat Liver as Derived From the cDNA Sequence; Proc. Nat'l. Acad. Sci, USA; vol. 84, pp. 719–723, Feb. 1987.
Deguchi et al.; Inhibition of Transmethylations of Biogenic Amines by Adenosylhomocysteinase; The Journal of Biological Chemistry; vol. 10, pp. 3175–3318, 1971.
Jakubowski et al.; S–Adenosylhomocysteinase From Yellow Lupin Seeds: Stoichiometry and Reactions of the Enzyme–Adenosine Complex; Biochemistry 1 20, pp. 6877–6881, 1981.
Trezzini et al.; Isolation of Putative Defense–Related Genes From *Arabidopsis thaliana* and Expression in Fungal Elicitor–Treated Cells; Plant Molecular Biology; vol. 21, pp. 385–389, 1993.
Tanaka et al.; Inducible Expression by Plant Hormones of S–Adenosyl–L–Homocysteine Hydrolase Gene From *Nicotiana tabacum* During Early Flower Bud Formation In Vitro; Plant Science 113, pp. 167–174, 1996.
Skipsey et al.; The Cloning and Characterisation of S–Adenosyl–L–Homocysteine Hydrolase; Journal of Experimental Botany 45, 12, 1994.
Merta et al.; The Gene and Pseudogenes of Rat S–Adenosyl–L–Homocysteine Hydrolase; European Journal of Biochemistry; 229, pp. 575–582; Apr. 1995.

(List continued on next page.)

Primary Examiner—David T. Fox
Attorney, Agent, or Firm—Pillsbury Madison & Sutro, LLP

[57] ABSTRACT

A promoter derived from an SHH gene, especially the SHH gene of *Arabidopsis thaliana* which is capable of directing expression on a variety of operator genes in both monocotyledonous and dicotyledonous plants. The promoter of the invention may be used for directing expression of pathogen resistance genes to disease or wound sites.

12 Claims, 34 Drawing Sheets

OTHER PUBLICATIONS

Buggy et al.; Nucleotide Sequence and Characterization of the *Rhodobacter capsulatus* HvrB Gene: HvrB is an Activator of S–Adenosyl–L–Homocysteine Hydrolase Expression and is a Membrane of the LysR Family; Journal of Bacteriology 176, pp. 61–69, (1994).

Clarke et al.; High–Frequency Transformation of *Arabidopsis thaliana* by Agrobacterium Tumefaciens; Plant Molecular Biology Reporter; vol. 10, pp. 178–189 (1992).

Tabor et al.; Methionine Adenosyltransferase (S–Adenosylmethionine Synthetase) and S–Adenosylmethionine Decarboxylase; pp. 251–282.

Fig. IA

```
        CTCGTTTCAGATCGGATCTGAAGAAATGGCTCTCCTCGTTGAGAAGACTACCTCTGGCCG
   1    ------+---------+---------+---------+---------+---------+   60
        GAGCAAAGTCTAGGCTAGACTTCTTTACCGAGAGGAGCAACTCTTCTGATGGAGACCGGC
                          M  A  L  L  V  E  K  T  T  S  G  R

CGAGTACAAGGTCAAGGACATGTCTCAGGCCGACTTCGGCCGTGAAGCTCGC
  61    ------+---------+---------+---------+---------+---------+  120
        GCTCATGTTCCAGTTCCTGTACAGAGTCCGGCTGAAGCCGGCACTTCGAGCG
         E  Y  K  V  K  D  M  S  Q  A  D  F  G  R  L  E  I  E  L  A

TGAGGTCGAGATGCCAGGGCTCATGGCCTGCCGTGCCGAGTTCGGCCCCGCCCAGCCATT
 121    ------+---------+---------+---------+---------+---------+  180
        ACTCCAGCTCTACGGTCCCGAGTACCGGACGGCACGGCTCAAGCCGGGGCGGGTCGGTAA
         E  V  E  M  P  G  L  M  A  C  R  A  E  F  G  P  A  Q  P  F
                            BamHI

CAAGGGCGCAAAAATCACTGGATCCCTCCACATGACGATCCAAACTGCCGTCCTCATCGA
 181    ------+---------+---------+---------+---------+---------+  240
        GTTCCCGCGTTTTTAGTGACCTAGGGAGGTGTACTGCTAGGTTTGACGGCAGGAGTAGCT
         K  G  A  K  I  T  G  S  L  H  M  T  I  Q  T  A  V  L  I  E
                                                  PCR-1 Primer
        AACCCTAACCGCCCCTCGGGCCCCGAGGTTCGCTGGTGTCCTGCAACATATTCTCCACCCA
 241    ------+---------+---------+---------+---------+---------+  300
        TTGGGATTGGCGGGGAGCCCGGGGCTCCAAGCGACCACAGGACGTTGTATAAGAGGTGGGT
```

Fig. IB

```
      T  L  T  A  L  G  P  E  V  R  W  C  S  C  N  I  F  S  T  Q
      GGACCATGGCGCCGCTGCCATTGCCCCTGACTTCCGCCTCTTCGCCTCTGAAGGGTGA
301   ---------+---------+---------+---------+---------+---------+   360
      CCTGGTACGCGGCGGACGGTAACGGGACACTGAGGCGGAGGCAGAAGCGGACTTCCCACT

D  H  A  A  A  I  A  R  D  S  A  S  V  F  A  W  K  G  E
      GACCCTCCAGGAGTACTGGTGTGCACCGAGCGTGCCCTCGACTGGGCCCCGGCGGTGG
361   ---------+---------+---------+---------+---------+---------+   420
      CTGGGAGGTCCTCATGACCACACGTGGCTCGACGGAGCTGACCCGGGGCCGCCACC

T  L  Q  E  Y  W  C  T  E  R  A  L  D  W  G  P  G  G  G
      CCCTGACCTCATCGTCGATGACGGCGGCGACACCACTCTCTTGATCCATGAGGGGTGAA
421   ---------+---------+---------+---------+---------+---------+   480
      GGGACTGGAGTAGCAGCTACTGCCGCCGCTGTGGTGAGAGAACTAGGTACTCCCCACTT

P  D  L  I  V  D  D  G  G  D  T  T  L  L  I  H  E  G  V  K
      GGCCCGAGGAAGAGTACGAGAAGACGGGGAAGATGCCCGATCCGGCGTCTACCGACAATGC
481   ---------+---------+---------+---------+---------+---------+   540
      CCGGCTCCTTCTCATGCTCTTCTGCCCCTTCTACGGGCTAGGCCGAGATGGCTGTTACG

```
       TGAGTTCCAGATCGTGCTCACAATCATCAGGGATGGGCTCAAGGTGGACCCCACCAAGTA
541    ------+---------+---------+---------+---------+---------+   600
       ACTCAAGGTCTAGCACGAGTGTTAGTAGTCCCTACCCGAGTTCCACCTGGGGTGGTTCAT p   E  F  Q  I  V  L  T  I  I  R  D  G  L  K  V  D  P  T  K  Y  -

CAGGAAGATGAAGGATAGGATTGTGGTGTGTCGGAGAGAGACCACCACCGGGGTCAAGAG
601    ------+---------+---------+---------+---------+---------+   660
       GTCCTTCTACTTCCTATCCTAACAGCCACACAGCCTCTCTGGTGGTGGCCCCAGTTCTC p   R  K  M  K  D  R  I  V  G  V  S  E  E  T  T  T  G  V  K  R  -

GCTTTACCAGATGCAGGCTAACAATTCCCTTCTTTTCCCTGCGATCAATGTCAATGACTC
661    ------+---------+---------+---------+---------+---------+   720
       CGAAATGGTCTACGTCCGATTGTTAAGGGAAGAAAAGGACGCTAGTTACAGTTACTGAG p   L  Y  Q  M  Q  A  N  N  S  L  L  F  P  A  I  N  V  N  D  S  -

CGTCACCAAGAGCAAGTTTGACAATCTGTATGGATGCCGGCACTCTCTTCCCGATGGTCT
721    ------+---------+---------+---------+---------+---------+   780
       GCAGTGGTTCTCGTTCAAACTGTTAGACATACCTACGGCCGTGAGAGAAGGGCTACCAGA
              PCR-2 Primer p   V  T  K  S  K  F  D  N  L  Y  G  C  R  H  S  L  P  D  G  L  -

GATGAGGGCCACTGATGTTATGATTGCTGGCAAGGTTGCAGTTGTCTGCGGTTATGGTGA
781    ------+---------+---------+---------+---------+---------+   840
       CTACTCCCGGTGACTACAATACTAACGACCGTTCCAACGTCAACAGACGCCAATACCACT p   M  R  A  T  D  V  M  I  A  G  K  V  A  V  V  C  G  Y  G  D  -
```

Fig. 1D

```
      TGTCGGAGAGGGCTGTGTGCTGCACTCAAGCAGGCTGGTGCCCGTGTTATTGTGACGGA
 841  ------+---------+---------+---------+---------+---------+  900
      ACAGCCTCTCCCGACACACGACGTGAGTTCGTCCGACCACGGGCACAATAACACTGCCT

V  G  E  G  C  A  A  A  L  K  Q  A  G  A  R  V  I  V  T  E
                                                        XhoI
      GATCGACCCCATCTGTGCTCAGGGCGGATATCTTTGTTACCACCGGTAACAAGGACATCAT
 901  ------+---------+---------+---------+---------+---------+  960
      CTAGCTGGGTAGACACGAGAAGTTCGGGATTACCTCCCAGAAGTCCAGGAGTGGGAGCT

I  D  P  I  C  A  L  Q  A  L  M  E  G  L  Q  V  L  T  L  E

GGATGTGTCTCAGAGGCGGATATCTTTGTTACCACCGGTAACAAGGACATCATCAT
 961  ------+---------+---------+---------+---------+---------+ 1020
      CCTACAACAGAGTCTCCGCCTATAGAAACAATGGTGGCCATTGTTCCTGTAGTAGTA

D  V  V  S  E  A  D  I  F  V  T  T  G  N  K  D  I  I  M

GCTGGACCACATGAGGAAGATGAAGAACAATGCCATTGTCTGCAACATTGGTCACTTTGA
1021  ------+---------+---------+---------+---------+---------+ 1080
      CGACCTGGTGTACTCCTTCTACTTCTTGTTACGGTAACAGACGTTGTAACCAGTGAAACT

L  D  H  M  R  K  M  K  N  N  A  I  V  C  N  I  G  H  F  D

CAACGAGATTGACATGCTAGGTTTGGAGACATACCCTGGCATCAAGAGAATCACCATCAA
1081  ------+---------+---------+---------+---------+---------+ 1140
      GTTGCTCTAACTGTACGATCCAAACCTCTGTATGGGACCGTAGTTCTCTTAGTGGTAGTT

```
      GCCCCAGAGACTGACCGGTGGGTCTTCCCTGAAACCAACACTGGTATAATTGTTCTTGCTGA
1141  ------+---------+---------+---------+---------+---------+  1200
      CGGGGTCTGACTGGCCCACCCAGAAGGGACTTTGGTTGTGACCATATTAACAAGAACGACT

P  Q  T  D  R  W  V  F  P  E  T  N  T  G  I  I  V  L  A  E  -

GGGCCGACTCATGAACCTTGGGTGTGCCACTGGTCACCCCAGCTTTGTCATGTCCTGCTC
1201  ------+---------+---------+---------+---------+---------+  1260
      CCCGGCTGAGTACTTGGAACCCACACGGTGACCAGTGGGGTCGAAACAGTACAGGACGAG

G  R  L  M  N  L  G  C  A  T  G  H  P  S  F  V  M  S  C  S  -

CTTCACCAACCAGGTGATTGCTCAGCTAGAGTTGTGGAATGAGAAGGCAAGTA
1261  ------+---------+---------+---------+---------+---------+  1320
      GAAGTGGTTGGTCCACTAACGAGTCGATCTCAACACCTTACTCTTCCGTTCGCCGTTCAT

F  T  N  Q  V  I  A  Q  L  E  L  W  N  E  K  A  S  G  K  Y  -

TGAGAAGAAGGTTTACGTGCTCCCCAAGCATCTTGATGAGAAAGTAGCAGCGCTTCACTT
1321  ------+---------+---------+---------+---------+---------+  1380
      ACTCTTCTTCCAAATGCACGAGGGGTTCGTAGAACTACTCTTTCATCGTCGCGAAGTGAA

E  K  K  V  Y  V  L  P  K  H  L  D  E  K  V  A  A  L  H  L  -
                                       HindIII
      GGGCAAGCTCGGAGCCAAGTTACAAAGTCAGCCCTTCACAGGCGGACTACATCAGCGT
1381  ------+---------+---------+---------+---------+---------+  1440
      CCCGTTCGAGCCTCGGTTCGAATGTTTCAGTCGGGAAGTGTCCGCCTGATGTAGTCGCA
```

```
         G  K  L  G  A  K  L  T  K  L  S  P  S  Q  A  D  Y  I  S  V  -
      CCCCATCGAGGGTCCCTACAAGCCACCTCACTACAGGTACTAGACGCTGTTGTGCCGGGG
1441  ---------+---------+---------+---------+---------+---------+ 1500
      GGGGTAGCTCCCAGGGATGTTCGGTGGAGTGATGTCCATGATCTGCGACAACACGGCCCC

P  I  E  G  P  Y  K  P  P  H  Y  R  Y  *
      AGAGATCATCGCAGCAAGAAAGTATTAAGATTGAAGAAGAGAGTTGTTATGGAGGACATG
1501  ---------+---------+---------+---------+---------+---------+ 1560
      TCTCTAGTAGCGTCGTTCTTTCATAATTCTAACTTCTTCTCTCAACATACCTCCTGTAC

GCTATATTTACTTTATTCCTACCTATTCTCTTGCTGTTTCTCTTCCGAACTTTTAGACT
1561  ---------+---------+---------+---------+---------+---------+ 1620
      CGATATAAATGAATAAAGGATAAGAACGACAAAGAGAAAGGCTTGAAAATCTGA

GATCCCTCTCTTGATTTATTACGATATGAATTCTGTTTAAATTTTGCTTATTCT
1621  ---------+---------+---------+---------+---------+---------+ 1680
      CTAGGAGAAGAGAAACTAAATAATGCTATACTTAAGACAAATTTAAAACGAATAAGA

CTAATGATGAGCTAGCAGACATATGTTCTGTGGTAGAATAACGAGGTTTTGAACTTTGTG
1681  ---------+---------+---------+---------+---------+---------+ 1740
      GATTACTACTCGATCGTCTGTATACAAGACA,CCATCTTATTGCTCCAAAACTTGAAACAC

CAAAAAAAAAAAAAAAAAAAAAAAAAA
1741  ---------+---------+------- 1767
      GTTTTTTTTTTTTTTTTTTTTTTTTTT
```

```
            1                                                           50
Dbf.Gap     MALLVEKTTS GREYKVKDMS QADFGRLEIE LAEVEMPGLM ACRAEFGPAQ
Pcshh.Gap   MALSVEKTAA GREYKVKDMS LADFGRLELE LAEVEMPGLM SCRTEFGPSQ 51                                                          100
Dbf.Gap     PFKGAKITGS LHMTIQTAVL IETLTALGPE VRWCSCNIFS TQDHAAAAIA
Pcshh.Gap   PFKJARITGS LHMTIQTGVL IETLTALGAE VRWCSCNIFS TQDHAAAAIA 101                                                         150
Dbf.Gap     RDSASVFAWK GETLQEYWWC TERALDWGPG GGPDLIVDDG GDTTLLIHEG
Pcshh.Gap   RDSCAVFAWK GETLQEYWWC TERALDWGPD GGPDLIVDDG GDATLLIHEG 151                                                         200
Dbf.Gap     VKAEEEYEKT GKMPDPASTD NAEFQIVLTI IRDGLKVDPT KYRKMKDRIV
Pcshh.Gap   VKAEEEYKKS GAIPDPASTD NAEFQIVLSI IRDGLKSDPM KYHKMKDRLV
```

Fig. 2B

```
         201                                                                      250
Dbf.Gap  GVSEETTTGV KRLYQMQANN SLLFPAINVN DSVTKSKFDN LYGCRHSLPD
Pcshh.Gap GVSEETTTGV KRLYQMQQNG TLLFPAINVN DSVTKSKFCN LYGCRHSLPD 251                                                                      300
Dbf.Gap  GLMRATDVMI AGKVAVVCGY GDVGEGCAAA LKQAGARVIV TEIDPICALQ
Pcshh.Gap GLMRATDVMI AGKVALIAGY DGVGKGCAAA MKQAGARVIV TEIDPICALQ 301                                                                      350
Dbf.Gap  ALMEGLQVLT LEDVVSEADI FVTTTGNKDI IMLDHMRKMK NNAIVCNIGH
Pcshh.Gap ATMEGLQVLP LEDVVSEVDI FVTTTGNKDI IMVSDMRKMK NNAIVCNIGH 351                                                                      400
Dbf.Gap  FDNEIDMLGL ETYPGIKRIT IKPQTDRWVF PETNTGIIVL AEGRLMNLGC
Pcshh.Gap FDNEIDMLGL ETYPGVKRIT IKPQTDRWVF PDTGRGIIIL AEGRLMNLGC 401                                                                      450
Dbf.Gap  ATGHPSFVMS CSFTNQVIAQ LELWNEKASG KYEKKVYVLP KHLDEKVAAL
Pcshh.Gap ATGHPSFVMS CSFTNQVIAQ LELWNEKSSG KYEKKVYVLP KHLDEKVAAL 451                              485
Dbf.Gap  HLGKLGAKLT KLSPSQADYI SVPIEGPYKP PHYRY
Pcshh.Gap HLGKLGAKLT KLSKDQADYI SVPVEGPYKP AHYRY
```

Fig. 3A

```
DBF     MALLVEKTTSGREYKVKDMSQADFGRLEIELAEVEMPGLMACRAEFGPAQPFKGAKITGS
PCSHH   MALSVEKTAAGREYKVKDMSLADFGRLELELAEVEMPGLMSCRTEFGPSQPFK-ARITGS
RCAHCY  MA---D------YIVKDIKLAEFGRKELDIAETEMPGLMACREEFGPSQPLKGARIAGS
RAT     MA---DKLP----YKVADIGLAAWGRKALDIAENEMPGLMRMREMYSASKPLKGARIAGC
CEHHG   MA---QSKFA---YKVADIKLADFGRKEIILAENEMPGLMAMRSKYGPSQPLKGARIAGC
         *    .      *  . *  :* **:**:::  : .. ****:  : .  ** **:  .

DBF     LHMTIQTAVLIETLTALGPEVRWCSSCNIFSTQDHAAAAIARDSASVFAWKGETLQEYWW-
PCSHH   LHMTIQTGVLIETLTALGAEVRWCSSCNIFSTQDHAAAAIARDSCAVFAWKGETLQEYWW-
RCAHCY  LHMTIQTAVLIETLKALGADVRWASCNIFSTQDHAAAAIAAGGTPVFAVKGETLEEY-WA
RAT     LHMTVETAVLIETLVALGAEVRWSSCNIFSTQDHAAAAIAKAGIPVFAWKGETDEEYLW-
CEHHG   LHMTIQTAVLIETLTALGAEVQWSSCNIFSTQDHAAAAIAQTGVPVYAWKGETDEEYEW-
        ****:.:*******.***.:*:* ************* .   .*:*.****  **  *

DBF     CTERALDWGPGGGPDLIVDDGGDTTLLIHEGVKAEEYEKTGKMPDPASTDNAEFQIVLT
PCSHH   CTERALDWGPDGGPDLIVDDGGDATLLIHEGVKAEEEYKKSGAIPDPASTDNAEFQIVLS
RCAHCY  YTDKIFQFPEGTC-NMILDDGGDATLYILLGARVEAG--ETDLIATPTSEDEV---CLFN
RAT     CIEQTLHFKDG-PLNMILDDGGDLT------------------------NLIHTK----
CEHHG   CIEQTIVFKDGQPLNMILDDGGDLT------------------------NLVHAK----
         :: .: :  .  ::::***** *                         :: :
```

Fig. 3B

```
DBF     IIRDGLKVDPTKYRKMKDRIVGVSEETTTGVKRLYQMQANNSLLFPAINVNDSVTKSKFD
PCSHH   IIRDGLKSDPMKYHKMKDRLVGVSEETTTGVKRLYQMQQNGTLLFPAINVNDSVTKSKFC
RCAHCY  QIKKRMVESPGWFTQQRAAIKGVSEETTTGVHRLYDLHKKGLLPFPAINVNDSVTKSKFD
RAT     ---------HPQLLSGIRGISEETTTGVHNLYKMANGILKVPAINVNDSVTKSKFD
CEHHG   ---------YPQYLAGIRGLSEETTTGVHNLAKMLAKGDLKVPAINVNDSVTKSKFD
         .       ::* *:*******:.  :: :  : .* :*************

DBF     NLYGCRHSLPDGLMRATDVMIAGKVAVVCGYGDVGEGCAAALKQAGARVIVTEIDPICAL
PCSHH   NLYGCRHSLPDGLMRATDVMIAGKVALIAGYDGVGKGCAAAMKQAGARVIVTEIDPICAL
RCAHCY  NKYGCKESLVDGIRRATDVMMAGKVAVVCGYGDVGKGSAAASLRGAGARVKVTEVDPICAL
RAT     NLYGCRESLIDGIKRATDVMIAGKVAVVAGYGDVGKGCAQALRGFGARVIIEIDPINAL
CEHHG   NLYGIRESLPDGIKRATDVMLAGKVAVVAGYGDVGKGSAASLKAFGSRVIVTEIDPINAL
         * **  .** **: *****:.*****:: ** **:*.* :: . .:*  *:::**.**

DBF     QALMEGLQVLTLEDVVSEADIFVTTTGNKDIIMLDHMRKMKNNAIVCNIGHFDNEIDMLG
PCSHH   QATMEGLQVLPLEDVVSEVDIFVTTTGNKDIIMVSDMRKMKNNAIVCNIGHFDNEIDMLG
RCAHCY  QAAMDGFEVVVLEDVVADADIFITTTGNKDVIRIEHMREMKDMAIVGNIGHFDNEIQVAA
RAT     QAAMEGYEVTTMDEACKEGNIFVTTGCVDIILGRHFEQMKDDAIVCNIGHFDVEIDVKW
CEHHG   QAAMEGYEVTTLEEAAPKANIIVTTGCKDIVTGKHFELLPNDAIVCNVGHFDCEIDVKW
         ** *:*::*  :: .  . :*::**  .*:       : .:. ** *:***. * 
```

Fig. 3C

```
DBF      LETYPGIKRITIKPQTDRWVFPETNTGIIVLAEGRLMNLGCATGHPSFVMSCSFTNQVIA
PCSHH    LETYPGVKRITIKPQTDRWVFPDTGRGIILAEGRLMNLGCATGHPSFVMSCSFTNQVIA
RCAHCY   LKN-H--KWTNIKDQVDMIEMPSGAR-IILLSEGRLLNLGNATGHPSFVMSASFTNQVLA
RAT      LNE-NAVEKVNIKPQVDRYLLKNGHR-IILLAEGRLVNLGCAMGHPSFVMSNSFTNQVMA
CEHHG    LNT-NATKKDTIKPQVDRYTLKNGRH-VILLAEGRLVNLGCATGHPSFVMSNSFTNQVLA
             .  .  **:***.  . *:  :*:*  ::*:***:***.: ****:***.*****:*

DBF      QLELWNE-KASGKYEKKVYVLPKHLDEKVAALHLGKLGAKLTKLSPSQADYISVPIEGPY
PCSHH    QLELWNE-KSSGKYEKKVYVLPKHLDEKVAALHLGKLGAKLTKLSKDQADYISVPVEGPY
RCAHCY   QIELWTK---GAEYQPGVYILPKSLDEKVARLHLKKIGVKLTTLRPDQAEYIGVTVEGPF
RAT      QIELWTH---PDKYPVGVHFLPKKLDEAVAEAHLGKLNVKLTKLTEKQAYLGMPINGPF
CEHHG    QVELWTKFGTPQEYKLGLYVLPKTLDEEVAYLHLAQLGVKLTKLSDEQASYLGVPVAGPY
          :***.    . : :  :::** ***.**  **  :* **  *   :* :   : **:

DBF      KPPHYRY
PCSHH    KPAHYRY
RCAHCY   KSDHYRY
RAT      KPDHYRY
CEHHG    KPDHYRY
         *  ****
```

Fig. 4A

```
ASP    HAAAAIARDSASVFAWKGETLQEYWCTERAL-----DWGPGGGPDLIVDDGGDTTLL-I
ARA    HAAAAIARDSAAVFAWKGETLQEYWCTERAL-----DWGPGGGPDLIVDDGGDATLFRI
TOB    HAAAAIARDSRAVFAWKGETLQEYWCTERAL-----DWGPGGGPDLIVDDGGDATLL-I
BR     HAAAAIARDSAAVFAWKGETLEEYWCTERCL-----DWGVGGGPDLIVDDGGDPTLL-I
WHU    RAAAAIARDSASVFAWKGETLQGYWCTERAL-----DWGPGGGLDLIVDDGGDTTLL-I
WH     QAAAAIAAAGIPVFAWKGETEEEYEWCIEQTILKDGKPW----DANMVLDDGGDLT---
              .    ::::::::: .  : .     .:  :: :::::: .

ASP    HEGVKAEEEYEKTGKMPDPASTDNAEFQIVLTIIRDGLKVDPTKYRKMKDRIVGVSEETT
ARA    HEGVKAEEIFEKTGQVPDPTSTDNPEFQIVLSIIKEGLQVDPRKYHKMKERLVGVSEETT
TOB    HEGVKAEEEYAKSGKLPDPSSTDNVEFQLVLTIIRDGLKTDPLKYTEMKERLVGVSEETT
BR     HEGVKAEEFEKSGKIPDPESADNPEFKIVLTIIRDARKYRKMKERLVGVSEETT
WHU    HEGVKAEEEYEKTGKMPDPTSTDNAEFQIVLTIIRDGLKVDPTKYRKMKDRIVGVSEETT
WH     ------EILHK----------------------------KYPQMLERIHGITEETT
             :                                          :::

ASP    TGVKRLYQMQANNSLLFPAINVND-
ARA    TGVKRLYQMQENGTLLFPAINVNDS
TOB    TGVKRLYQMQANGTLLFPAINVNDS
BR     TGAKRLYQTQNPGTLLFPAINVNDS
WHU    TGVKRLYQMQANNSLLFLTINVNDS
WH     TGVHRLLDMLKAGTLKVPAINVNNA
       :: :::   :  ..*::::::*. 
```

Fig.4B

```
ASP  HAAAAIARDSASVFAWKGETLQEYWCTERALDWGPGGGPDLIVDDGGDTTLL-IHEGVK
ARA  HAAAAIARDSAAVFAWKGETLQEYWCTERALDWGPGGGPDLIVDDGGDATLFRIHEGVK
TU   HAAAAIARDSRAVFAWKGETLQEYWCTERALDWGPGGGPDLIVDDGGDATLL-IHEGVK
BR   HAAAAIARDSAAVFAWKGETLEEYWCTERCLDWGVGGGPDLIVDDGGDPTLL-IHEGVK
WHU  RAAAAIARDSASVFAWKGETLQGYWCTERALDWGPGGGLDLIVDDGGDTTLL-IHEGVK
        :****:***:.**********:*:***** ***** * :****** . ******

ASP  AEEEYEKTGKMPDPAASTDNAEFQIVLTIIRDGLKVDPTKYRKMKDRIVGVSEETTTGVKR
ARA  AEEIFEKTGQVPDPTSTDNPEFQIVLSIIKEGLQVDPRKYHKMKERLVGVSEETTTGVKR
TU   AEEEYAKSGKLPDPSSTDNVEFQLVLTIIRDGLKTDPLKYTEMKERLVGVSEETTTGVKR
BR   AEEEFEKSGKIPDPESADNPEFKIVLTIIRDGLKTDARKYRKMKERLVGVSEETTTGAKR
WHU  AEEEYEKTGKMPDPTSTDNAEFQIVLTIIRDGLKVDPTKYRKMKDRIVGVSEETTTGVKR
     *** : *:.::***  :** **::**:**::**: *  ** :**:*:********.**

ASP  LYQMQANNSLLFPAINVNDS
ARA  LYQMQENGTLLFPAINVNDS
TU   LYQMQANGTLLFPAINVNDS
BR   LYQTQNPGTLLFPAINVNDS
WHU  LYQMQANNSLLFLTINVNDS
     *** *  .:***  ******
```

Fig. 5A

```
  1 CTCGAGTGTT GACCTTTTCT GGTCGATTGA ATAGAATCGA ATGTCTTAAT
 51 CCAGTACCCT CCAGCTTTTA TTTCGTGTAA TTTATTTTCC AAACCTACCA
101 CTACCAGTTT CATAACTCTC GAATAAATTT ATCAAATAGT CTTTTGAGTG
151 CTCAAAGTCT TGGGATAATA AATGGTCAGT GCTATGTATC ACCCGGATGT
201 GAAACATTAT GGGTGGAGAT AGACTATTAT AAATTTATTG AAATATACGA
251 TTGTTACTCG TTTAATAGCA AAAGTAGTAC AATGTATATA GTTTCTATCG
301 AGAACAAGAT CTATTTAAAA TTCGAAAAGT ACATTTAAAA TTCATAAACA
351 TATAAAGATA GTAACATGTT AGATCTGCAT AGTACCACCA AAACAAGAAA
401 AAAGAAACGC ACATCGCCAC ATAATTGCTA TGATTCTCAC TGTCGGCTGC
451 TTTGAAATAT TCGATTCTTT TGGTAAATCA CACAACATAA TATAATTACA
501 ATAAATATAT ATATACTAAA TATAATTAA GTATAATTAA TATAATTAAT ACCACATTGT
551 TTAATTCTGT TTTGATCTTT TAAGATCAGT CAGATCCACC GACGTTCCTA
601 CACGGCCAGG TCCAGATCCA AACAGCACAC ACACACACAC AATGCCACTA
651 GTGTAAATGC TTGGTGGCTA TTGCATTTGC ACCTATTGAT ACTCTTTCTT
701 CAAAAACAAG TTATTGTTTT TATTTTCAAC CCAACTTTAA TACGGATTCA
```

Fig. 5B

```
 751   TACTGGGATT TAGGTGTTAA ATCTGATAAT TTAGGTTTGA ATAAGTTGTA
 801   TATTTGTTTC TTTGATTAAA AAAAGAACCT ATATATATAC AAAAATAAAT
 851   AAAAAGTTCT AGATTTCAAT TTTCCGTATA TAGCGGGTTG AATTGTCTAT
 901   TTTAATATGA AAATTGXCGG ATCTTATAAA CAAAATGTTC TGAAATATGT
 951   AAAAGGATTT AGCCAAAGTT AACCAAAAAA AAAAAAAACAA ACAGAAAAGT
1001   CACATTCACA TGTCGTGGTA GATCTAAGGC ATTAATTTAG AAATATGTCG
1051   TTACAATAAG CGGAGAACAT GGGACGTTTC TCGTGGTCCA ATCAGACGAA
1101   CGAGATCTCA TAAATTAAAT GACTTCAGXC GAGGGAATTC ATGGCAGAAT
1151   GATAATGCAA CTTAAGTGAC TTTAGAGTGA AAATGATACG AGAACAATGC
1201   ATAATCCATA TGACCGTTGA GTGAGTGATA CCATTAGCGC GATACAAGCG
1251   GGACTATAAA CTGATCTAGA TTGTTTTTCT TGGGAAAAAA TGTTACAAAT
1301   TTTAAATATG TAGTTTGAAT TGTTAAACCA AGATTCAACA GAAATATACC
1351   GTAAATAAAC AACAGTTGAT AATAGTCATC GAAAAGATAT CAACTGATTC
1401   TTCACTTGGG CTACTGTGAC GGCCGTTAG GTTCTCAATA TAAGTCAATA
1451   ACTACGATCT ACGATTCACT GAAACAAATA AAACACAGCC ACGTGTCCAC
```

Fig. 5C

```
1501  CCTCCCACAT CACCGTCCGA TCTAACCCAC GACAAGCTTA CAACACGGGT
1551  CATACCGGCT CGTGCAGGGT GTTCCGTCAT CCACGGGATT ACAACTTCTA
1601  CCAGATCCAC CAAACCCTCA AAACAATCTG AACCGTTCAT TTCATTTTGA
1651  CCTCATCTAT ATATTCTCTG TCACTCCCCT TTCTCTTCTC CTCGCACACA
1701  CTTCTCTCTC TCTCTCTCTC TGCCTCCTTT CGGATTCAAA TCTCAGATCT
                                          Met
1751  AGCTCAACCA TG CCGTTGCT CGTCGAGAAG ACCTCAAGTG GCCGTGAATA
1801  CAAGGTCAAA GACATGTCTC AAGCCGATTT CGGTCGTCTC GAACTCGAG
```

Fig. 6A

```
     ATGGCGTTGCTCGTCGAGAAGACCTCAAGTGCCGTGAATACAAGGTCAAAGACATGTCT
1760 +---------+---------+---------+---------+---------+---------+ 1819
     TACCGCAACGAGCAGCTCTTCTGGAGTTCACGGCACTTATGTTCCAGTTTCTGTACAGA

G  V  A  R  R  E  D  L  K  W  P  *  I  Q  G  Q  R  H  V  S  -
      M  A  L  L  V  E  K  T  S  S  G  R  E  Y  K  V  K  D  M  S  -
      W  R  C  S  *  R  R  P  Q  V  A  V  N  T  R  S  K  T  C  L
                          x
                          h
                          o
                          I

CAAGCCGATTTCGGTCGTCTCGAACTCGAGCTCGCCGAAGTTGAGATGCCTGGACTCATG
1820 +---------+---------+---------+---------+---------+---------+ 1879
     GTTCGGCTAAAGCCAGCAGAGCTTGAGCTCGAGCGGCTTCAACTCTACGGACCTGAGTAC

S  R  F  R  S  S  R  T  R  A  R  R  S  *  D  A  W  T  H  G  -
      Q  A  D  F  G  R  L  E  L  E  L  A  E  V  E  M  P  G  L  M  -
      K  P  I  S  V  V  S  N  S  S  S  P  K  L  R  C  L  D  S  W
                          E
                          c
                          o
                          R
                          I

GCTTGTGTCGTACCGAATTCGGACCTTCTCAGGCATTCAAAGGCGCTAGAATCACCGGATCT
1880 +---------+---------+---------+---------+---------+---------+ 1939
     CGAACAGCATGGCTTAAGCCTGGAAGAGTCCGTAAGTTTCCGCGATCTTAGTGGCCTAGA
```

CTTCACATGACCATCCAAACCGCCGTACTCATCGAAACCCTAACTGCTCTCGGTGCTGAA
1940 +----+----+----+----+----+----+----+----+----+----+----+----+ 1999
     GAAGTGTACTGGTAGGTTTGGCGGCATGAGTAGCTTTGGGATTGACGAGAGCCACGACTT a    S  H  D  H  P  N  R  R  T  H  R  N  P  N  C  S  R  C  *  S  -
b    L  H  M  T  I  Q  T  A  V  L  I  E  T  L  T  A  L  G  A  E  -
c    F  T  *  P  S  K  P  P  Y  S  S  K  P  *  L  L  S  V  L  K  -

GTCAGATGGTGTTCCTGCAACATCTTTTCCACTCAAGACCACGCCGCCAGCCATCGCT
2000 +----+----+----+----+----+----+----+----+----+----+----+----+ 2059
     CAGTCTACCACAAGGACGTTGTAGAAAAGGTGAGTTCTGGTGCGGCGGTCGGTAGCGA a    Q  M  V  F  L  Q  H  L  F  H  S  R  F  R  R  R  S  H  R  S  -
b    V  R  W  C  S  C  N  I  F  S  T  Q  D  H  A  A  A  A  I  A  -
c    S  D  G  V  P  A  T  S  F  P  L  K  T  T  P  P  Q  P  S  L  -

CGTGACTCCGCCGCTGCTTTCGCCTGGAAAGGTGAGACTCTTCAGGAGTACTGGTGGTGT
2060 +----+----+----+----+----+----+----+----+----+----+----+----+ 2119
     GCACTGAGGCGGCGACGAAAGCGGACCTTTCCACTCTGAGAAGTCCTCATGACCACCACA a    *  L  R  R  C  F  R  L  E  R  *  D  S  S  G  V  L  V  V  Y  -
```

```
                R  D  S  A  A  A  F  A  W  K  G  E  T  L  Q  E  Y  W  W  C  -
                V  T  P  P  L  L  S  P  G  K  V  R  L  F  R  S  T  G  G  V  -
            ACCGAGGCTGCTCTAGATTGGGGTCCAGGTGTGGTCCTGATCTGATTGTTGATGATGGT
       2120 +---------+---------+---------+---------+---------+---------+ 2179
            TGGCTCGCACGAGATCTAACCCCAGGTCCACCACCAGGACTAGACTAACAACTACTACCA
                         x
                         b
                         a
                         I
                P  A  C  S  R  L  G  S  R  W  W  S  *  S  D  C  *  W  W  -
                T  E  R  A  L  D  W  G  P  G  G  G  P  D  L  I  V  D  D  G  -
                *  P  S  V  L  *  I  G  V  Q  V  V  L  I  *  L  L  M  M  V  -
            GGTGACGCTACTCTTTTGATTCATGAGGGTGTTAAAGCTGAGGAGATCTTTGAGAAGACT
       2180 +---------+---------+---------+---------+---------+---------+ 2239
            CCACTGCGATGAGAAAACTAAGTACTCCCACATTTCGACTCCTCTAGAAACTCTTCTGA
                *  R  Y  S  F  D  S  *  G  C  *  S  *  G  D  L  *  E  D  W  -
                G  D  A  T  L  L  I  H  E  G  V  K  A  E  E  I  F  E  K  T  -
                V  T  L  L  F  *  F  M  R  V  L  K  L  R  R  S  L  R  R  L  -
            GGTCAAGTTCCTGATCCTACTTCTACTGATAACCCTGAGTTTCAGATCGTGTTGTCTATT
       2240 +---------+---------+---------+---------+---------+---------+ 2299
            CCAGTTCAAGGACTAGGATGAAGATGACTATTGGGACTCAAAGTCTAGCACACAACAGATAA
                G  S  S  S  *  S  Y  F  Y  *  *  P  *  V  S  D  R  V  V  Y  -
                G  Q  V  P  D  P  T  S  T  D  N  P  E  F  Q  I  V  L  S  I  -
                V  K  F  L  I  L  L  L  I  T  L  S  F  R  S  C  C  L  L  -
```

```
                    GATAGGCTTAACAACAACATAATCACTAAGTAGAAGCAAGCTTTCATTGTTGGTTGTTG
2540   +---------+---------+---------+---------+---------+---------+   2599
                    CTATCCGAATTGTTGTTGTTATTAGTGATTCATCTTCGTTCGAAAAGTAACAACCAACAAC a      *  A  *  Q  Q  H  N  H  *  V  E  A  S  F  S  L  L  V  V  E  -
     b      D  R  L  N  N  N  I  T  K  *  K  Q  A  F  H  C  W  L  L  -
     c         I  G  L  T  T  *  S  L  S  R  S  K  L  F  I  V  G  C  *  -

AAAGTATTACGATCTAGTAGAGAAAAGTCCTCCTTGTTACAGAATTGCATGAAAAGT
2600   +---------+---------+---------+---------+---------+---------+   2659
                    TTTCATAATGCTAGATCATCTCTTTTCAGGAGGAACCAATGTCTTAAACGTACTTTTCA a      S  I  T  I  *  R  K  V  L  P  W  L  Q  N  L  H  E  K  S  -
     b      K  V  L  R  S  S  R  E  K  S  F  L  G  Y  R  I  C  M  K  S  -
     c      K  Y  Y  D  L  V  E  K  S  P  S  L  V  T  E  F  A  *  K  V  -

CAATATTTCTCATGCTTTCTTTGATTTTATATTCAACGTTTTGTTTACACTTATGTGCTG
2660   +---------+---------+---------+---------+---------+---------+   2719
                    GTTATAAAGAGTACGAAAGAAACTAAAATATAAGTTGCAAAACAAATGTGAATACACGAC a      I  F  L  M  L  S  L  I  L  Y  S  T  F  C  L  H  L  C  A  V  -
     b      Q  Y  F  S  C  F  L  *  F  Y  I  Q  R  F  V  Y  T  Y  V  L  -
     c      N  I  S  H  A  F  F  D  F  I  F  P  N  V  L  F  T  L  M  C  C  -
```

Hind III

```
       ACCATTGGTCACTTTGACAATGAGATTGACATGCCTGGACTTGAGACTTACCCTGGTGTG
3080   +---------+---------+---------+---------+---------+---------+  3139
       TGGTAACCAGTGAAACTGTTACTCTAACTGTACGGACCTGAACTCTGAATGGGACCACAC

H  W  S  L  *  Q  *  D  *  H  A  W  T  *  D  L  P  W  C  E  -  a
        T  I  G  H  F  D  N  E  I  D  M  P  G  L  E  T  Y  P  G  V  -  b
        P  L  V  T  L  T  M  R  L  T  C  L  D  L  R  L  T  L  V  *  -  c

AAGCGTATCACCATCAAGCCACAGACTGACAGGTGGGTGTTCCCAGAGACCAAGGCTGGA
3140   +---------+---------+---------+---------+---------+---------+  3199
       TTCGCATAGTGGTAGTTCGGTGTCTGACTGTCCACCACAAGGGTCTCTGGTTCCGACCT

A  Y  H  H  Q  A  T  D  *  Q  V  G  V  P  P  R  D  Q  G  W  N  -  a
        K  R  I  T  I  K  P  Q  T  D  R  W  V  F  P  E  T  K  A  G  -  b
        S  V  S  P  S  S  H  R  L  T  G  G  C  S  Q  R  P  R  L  E  -  c

ATCATTGTCTTGGCTGAGGGTCGTCTGATGAACTTGGGTGTCCCACTGTCACCCAAGT
3200   +---------+---------+---------+---------+---------+---------+  3259
       TAGTAACAGAACCGACTCCCAGCAGACTACTTGAACCACAGGTGACAGTGGGTTCA

H  C  L  G  *  G  S  S  D  E  L  G  L  S  H  W  S  P  K  F  -  a
        I  I  V  L  A  E  G  R  L  M  N  L  G  C  P  T  G  H  P  S  -  b
        S  L  S  W  L  R  V  V  *  T  W  V  V  P  L  V  T  Q  V  -  c

TTCGTGATGTCTTGCTCTTTCACCAACCAGGTGATTGCCCACCTCGAGCTCTGAACGAG
3260   +---------+---------+---------+---------+---------+---------+  3319
       AAGCACTACAGAACGAGAAGTGGTTGGTCCACTAACGGTGGAGCTCGAGACCTTGCTC
```

```
          TCCACGCTCCCAGAAAACTTG
    3680 --------------------- 3700
          AGGTGCGAGGGTCTTTTGAAC
```

```
              H  A  I  K  K  L   -
              S  T  L  P  I  N  I  -
              P  R  S  Q  K  T   -
```

Enzymes that do cut:

EcoRI    EcoRV   HindIII    SalI    XbaI    XhoI

Enzymes that do not cut:

BamHI    NotI

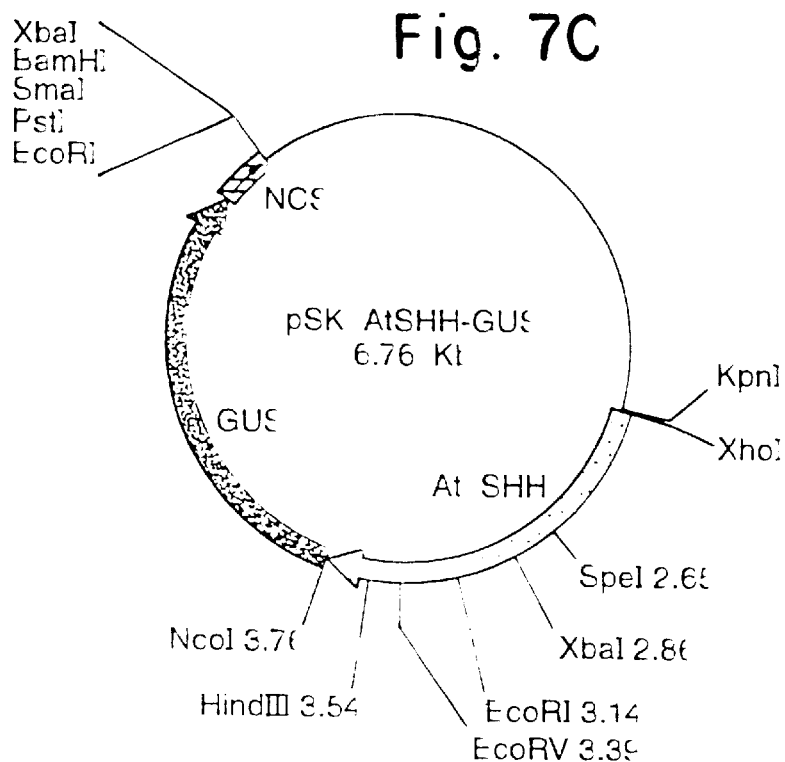
Fig. 7C
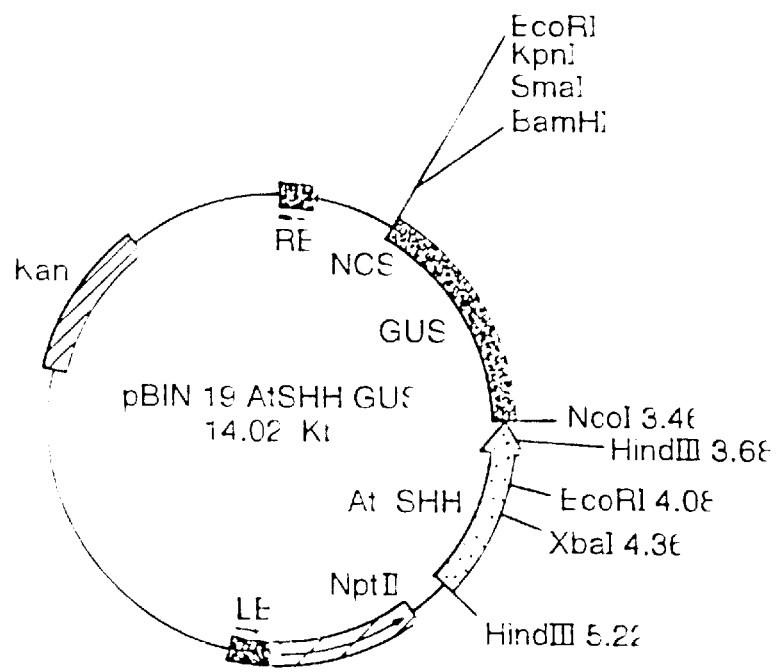

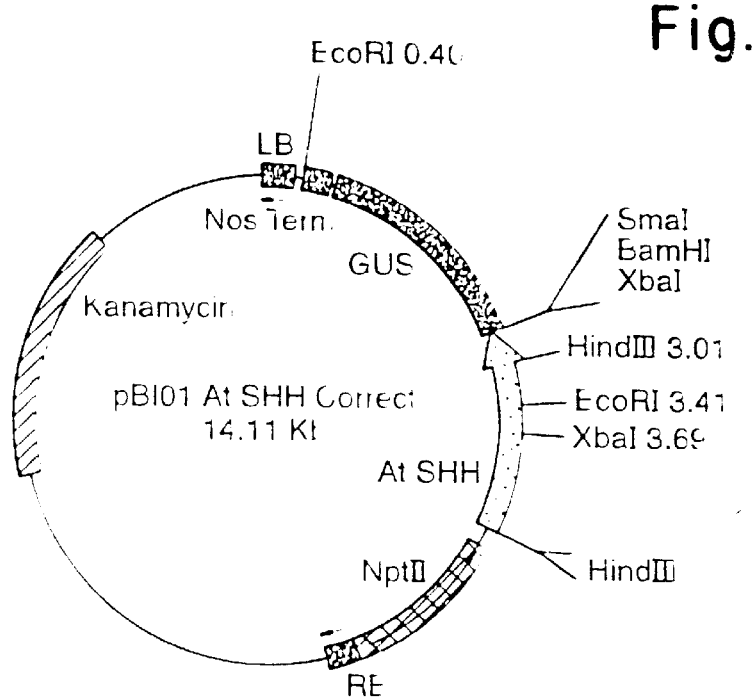
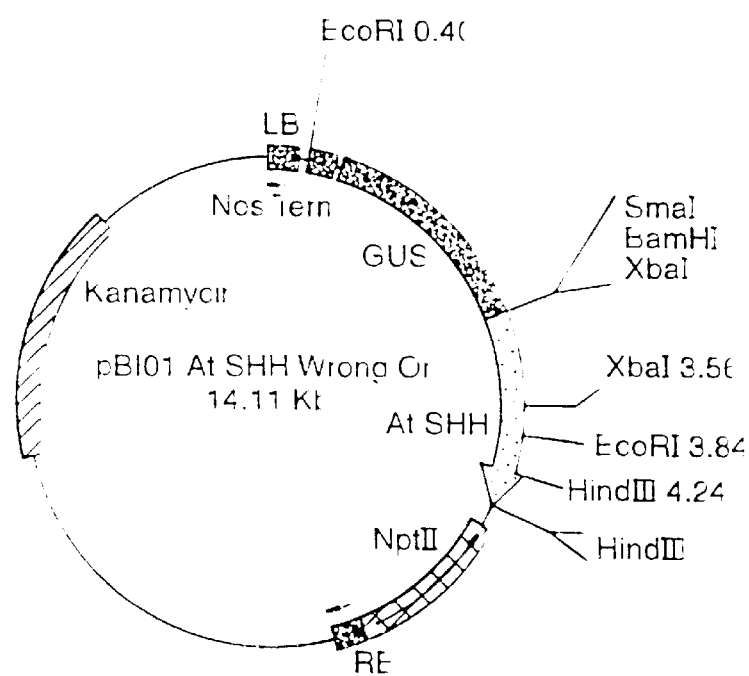
Fig. 7D

S-ADENOSYL-L-HOMOCYSTEIN HYDROLASE PROMOTER

This application is a 371 of PCT/GB/00882 filed Apr. 10, 1996.

FIELD OF THE INVENTION

The present invention relates to a promoter sequence capable of giving a high level of expression within plant cells. In particular, it relates to a promoter derived from a gene encoding S-adenosyl-L-homocysteine hydrolase (SHH).

BACKGROUND OF THE INVENTION

Promoters control the spatial and temporal expression of genes by modulating their level of transcription. Early approaches to genetically engineered crop plants utilised strong constitutive promoters to drive the expression of foreign genes. As strategies in plant biotechnology have become more sophisticated, specific promoters have been used to target transgene expression to a particular tissue or to a particular developmental stage. The promoter of the present invention is especially versatile as it can be used either to give constitutive expression of a gene or to target increased levels of gene expression at sites of wounding or pathogen invasion.

SHH was first described, in rat liver extracts, as the activity responsible for the reversible hydrolysis of S-adenosyl-L-homocysteine (SAH) to adenosine and homocysteine by the cleavage of a thioether bond in SAH [de la Haba, G. and Cantoni, G. L. (1959). *J. Biol. Chem.* 234, 603–608].

SAH is formed as a direct product of transmethylation reactions involving S-adenosyl-L-methionine (SAM) [Cantoni, G. L. and Scarano, E. (1954). *J. Am. Chem. Soc.* 76, 4744] and is known to be a potent inhibitor of most SAM mediated methyltransfer reactions. Therefore SAH is converted to homocysteine and adenosine by SHH as shown schematically below:

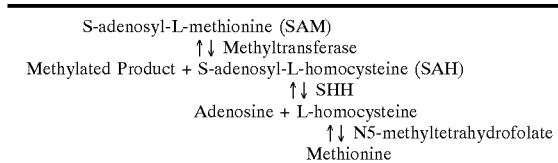

This pathway for the metabolism of SAH is the only pathway in most species. SHH has been found in all cells tested with the exception of *Escherichia coli* and other related bacteria [Shimzu, S. et al. (1984). *Eur. J. Biochem.* 141, 385–392].

The unique metabolic role of SHH in the removal of SAH and the structural complexity of the enzyme suggest that SHH may have a role in the regulation of the biological utilisation of SAM. SAM serves as a major methyl group donor for numerous highly specific methyltransferase reactions with a large variety of acceptor molecules; for example phenylpropanoid derivatives, cyclic fatty acids, proteins, polysaccharides and nucleic acids [Tabor, C. W. and Tabor, H. (1984). *Adv. Enzymol.* 56, 251–282]. It should be noted that SAM also has regulatory functions, namely the allosteric stimulation of threonine synthase. In plants, SHH has been studied primarily in relation to the biosynthesis of various phenylpropanoid derivatives.

Enzymes affecting the intracellular levels of SAH are important in the study of plant methylation reactions because it has been demonstrated that many methyltransferases are inhibited by SAH [Deguchi, T. and Barchos, J. (1971). *J. Biol. Chem.* 246, 3175–3181]. For example, an enzyme catalysing the methylation of caffeic acid was purified from spinach-beet leaves and found to be potently inhibited by SAH [Poulton, J. E. and Butt, V. S. (1976). *Arch. of Biochem. Biophys.* 172, 135–142]. Other metabolic pathways of the plant which involve transmethylation are the production of lignin and suberin, which are both derived from phenylalanine, through a series of reactions. These reactions include the methylation of caffeic acid into ferulic acid and also the methylation of s-hydroxyferulic acid into sinapic acid. Both these methylation reactions require SAM and hence produce SAH as a byproduct which needs to be removed by SHH to allow further transmethylation.

Once SHH had been isolated, many factors were calculated, such as the enzyme's pH optimum of 8.5, with a 50% activity between pH 6.5–10. Due to the Km value found for the substrate, L-homocysteine, the synthesis of SAH proceeds in vivo at a significant rate only when L-homocysteine is accumulated [Poulton, J. E. and Butt, V. S.(1976). *Arch. of Biochem. Biophys.* 172, 135–142].

In vivo, the adenosine produced by the hydrolysis of SAH is not deaminated but is converted to ADP by the successive action of adenosine kinase and adenylate kinase, both of which enzymes have been demonstrated in spinach-beet leaves. If L-homocysteine accumulates, it causes inhibition of SHH activity and therefore in vivo, L-homocysteine appears to be methylated by N5-methyltetrahydrofolate to methionine. Indeed, this reaction has been demonstrated in pea seedling extracts and spinach and barley leaves. Unlike all animal SHH enzymes, plant SHH is not inhibited by adenosine but is instead stabilised by low concentrations [Jakubowski, H. and Guranowski, A. (1981). *Biochem.* 20, 6877–6881].

The kinetic evidence shows that SHH is a sensitive regulator of SAH utilisation, its activity depending not only upon favourable concentrations of metabolites in relation to equilibrium conditions but also upon the levels of SAM, adenosine and L-homocysteine maintained within the system. These in turn will act as feed back inhibitors or activators to determine the rate of methylation reactions which are sensitive to the levels of SAH [Poulton, J. E. and Butt, V. S. (1976). *Arch. of Biochem. Biophys.* 172, 135–142].

As previously mentioned SHH has been found in all organisms tested except *E. coli* and some related species where a two step enzymatic process hydrolyses SAH into adenosine and L-homocysteine. So far the following SHH cDNAs have been isolated and published:

Rat [Ogawa, H. et al. (1987). *Proc. Natl. Acad. Sci. USA.* 84, 719–723],

*Dictostelium discoideum* [Kasir, J. et al. (1988). *Biochem. Biophys. Res. Commun.* 153, 359–364]

Human [Coulter-Karis, D. E. and Hershfield, M. S. (1989). *Ann. Hum. Genet.* 53, 169–175]

*Caenorhabditis elegans* [Prasad. S. S. et al. (1991). EMBL database Accession No. M64306]

*Leishmania donovani* [Henderson, D. M. and Ullman, B. (1992). EMBL database Accession No. M76556]

*Petroselinum crispum* [Kawalleck, P. et al. (1992). *Proc. Natl. Acad. Sci. USA.* 89, 4713–4717]

*Rhodobacter capsulatus* [Sganga, M. W. et al. (1992). *Proc. Natl. Acad. Sci. USA.* 89, 6328–6332]

The high level of homology between SHHs of evolutionary divergent species was highlighted further following isolation of SHH from the rat, from *Dictostelium discoideum*, from the purple non-sulphur photosynthetic bacterium *Rhodobacter capsulatus* and then from parsley (*Petroselinum crispum*). The bacterial SHH shows a remarkable degree of amino acid sequence homology, approximately 65% identity and 77% similarity to the previously isolated SHHs from rat, *D. discoideum*, human and *C. elegans*. This is one of the highest levels of sequence conservation ever reported between proteins having a similar function in prokaryotes and humans. Similarly, SHH cDNA from parsley is 64% identical to rat cDNA and there is 79% similarity at the amino acid level. The lack of sequence divergence between species may suggest a stringent requirement for SHH to retain its primary structure for function.

Both the *R. capsulatus* and the parsley amino acid sequences have an additional amino acid motif in comparison to the rat, *D. discoideum*, human, *C. elegans* and *L. donovani* sequences. *R. capsulatus* has an additional 36 amino acid region whereas parsley has an additional 41 amino acids. These two additional stretches are found in the same position in the predicted protein sequence, approximately one-third of the distance from the amino terminus. (see FIGS. 3A–3C) although they do not show significant homology.

SUMMARY OF THE INVENTION

The present inventors have now isolated SHH from various other plant sources. The first of these was *Asparagus officinalis* and the nucleotide sequence and deduced amino acid sequences for this (SEQ ID NO 1 and SEQ ID NO 2) together with the positions of the restriction sites are shown in FIGS. 1A–1F.

Asparagus SHH also contains the extra stretch of residues earlier found in the other photosynthetic species, parsley and *R. capsulatus* and not in SHH cDNAs from non-photosynthetic species. This 41 amino acid stretch, from amino acids 150 to 190 is as well conserved between the dicotyledon species parsley and the monocotyledon species asparagus as is the rest of the sequence although it is not similar to the 36 amino acid stretch from *R. capsulatus*. This is illustrated in FIGS. 2A, 2B, 3A–3C.

Following this, SHH cDNAs were also isolated from other species and one of the species selected was *Arabidopsis thaliana*. The promoter derived from the SHH gene from *A. thaliana* has proved to be particularly useful as it directs a high level of expression of a variety of genes, exemplifed by the reporter genes glucuronidase (GUS) and luciferase (LUC). Promoters from the SHH genes of other species may also be isolated using the same techniques and may also be expected to have useful and advantageous effects.

Therefore, in a first aspect of the present invention, there is provided a promoter derived from an SHH gene.

It is preferred that the SHH gene is that derived from *A. thaliana*.

The promoter has several useful properties and, in particular, because of the uniformity of the SHH gene over different species, it is capable of directing the expression of a wide variety of effect genes in plants, particularly crop plants such as Arabidopsis, tobacco, oil seed rape, potato, tomato, banana, wheat and maize.

The sequence of the Arabidopsis promoter (SEQ ID NO 3) is shown in FIGS. 5A–5C and thus in a second aspect of the invention, there is provided a promoter having the sequence of SEQ ID NO 3 or a sequence of at least 70% homology thereto.

It is preferred that the sequence of the promoter has not less than 80% homology, and, more preferably 90% homology to SEQ ID NO 3.

Since transmethylation reactions are important components of the biosynthetic machinery in most plant cells, the SHH will be expressed in cells throughout the plant. The promoter derived from the SHH will therefore provide a useful control mechanism for expression of any effect gene in a constitutive manner. The effect gene may be an SHH gene but will more usually be an introduced gene. Examples of introduced effect genes which may be linked to the promoter of the present invention include selectable markers such as NptII, the kanamycin resistance gene, the phosphinothricin resistance gene or the phosphinothricin acetyl transferase (PAT) gene and others such as the glucuronidase (GUS) and luciferase (LUC) reporter genes.

The predicted increase in transmethylation and concomitant increase in SHH activity following wounding or pathogen invasion means that the SHH gene will also be useful in providing increased levels of expression of introduced genes at sites of wounding and pathogen invasion. In this respect, the SHH promoter will be particularly useful for targeting expression of disease resistance genes, for example genes encoding antifungal proteins such as those described in our earlier patent applications published as WO92/15691, WO92/21699 and WO93/05 153. Using the SHH promoter, these antifungal proteins can be targeted to wound sites to prevent fungal invasion or to sites of infection to prevent further spread of the pathogen. The combined constitutive and wound/pathogen induced expression will thus provide a powerful mechanism for the prevention of disease using introduced genes.

In order to direct expression, the promoter and its associated effect gene must, of course be incorporated into a vector and therefore, in a further aspect of the invention there is provided a vector comprising the promoter of the present invention linked to an effect gene.

For expression in dicotyledonous plants binary agrobacterium vectors are particularly suitable whereas for monocotyledonous plants direct DNA delivery vectors are preferred.

As already mentioned above, the sequence of the SHH gene is conserved to a remarkable extent between species. The promoter of the present invention can therefore be used to direct expression in almost any plant species, whether monocotyledonous or dicotyledonous. It is of particular use in crop species such as wheat, maize, oil seed rape, potato, tomato, banana and tobacco.

Thus in a further aspect of the invention there is provided a plant cell transformed with a vector as described above. Transformation may be acheived by standard techniques.

The invention also provides a genetically transformed plant and parts thereof, such as cells protoplasts and seeds, having stably incorporated into the genome the construct of the present invention. Any plant may be chosen but the crop species listed above are particularly preferred.

As already mentioned, the expression of SHH at disease or wound sites means that the promoter will be of particular use in combating disease when linked to an appropriate effect gene.

Therefore, in a further aspect, the invention provides a method of increasing the resistance of a plant to infection by a pathogenic organism, the method comprising transforming the plant with a vector comprising a promoter according to the first aspect of the invention operably linked to a gene conferring resistance to the pathogenic organism.

Examples of genes conferring resistance to pathogenic organisms include the genes encoding antifungal proteins described in WO92/15691, WO92/21699 and WO93/05153.

The isolation of the promoter of the present invention was achieved as a result of the study of SHH in various plant species. The strategy employed was firstly to isolate the gene encoding asparagus SHH. This confirmed the remarkable degree of sequence identity in the SHH gene between plant species and was used as a basis for the design of polymerase chain reaction (PCR) primers which were used to isolate SHH genes from various other plant species including Arabidopsis thaliana. Analysis of the A. thaliana SHH gene revealed a 1849 base promoter, the promoter of the present invention, which, further experimentation demonstrated to be a highly versatile promoter capable of directing expression of different genes in a variety of plant species.

BRIEF DESCRIPTION OF THE DRAWINGS

The invention will now be further described for the purposes of illustration only with reference to the following examples and to the figures in which:

FIGS. 1A–F shows the nucleotide and deduced amino acid sequence of asparagus SHH (SEQ ID NOS 1 and 2). In FIGS. 1A–1F, the @ symbols define the positions of the start and finish of the original DB6 clone; the sites indicated were used for the sub-cloning of DB6 and the primers used in PCR experiments are underlined.

FIGS. 2A–2B comprise a comparison of full length predicted SHH protein from asparagus (Dbf) (SEQ ID NO 2) with SHH protein from parsley (Pcshh), the NAD⁻ binding site has been underlined in all species.

FIGS. 3A–3C comprise a comparison of SHH predicted amino acid sequence from asparagus (Dbf) with SHH proteins from rat, parsley (Pcshh), R. capsulatus (Rcahcy) and C. elegans (Cehcg); the NAD⁻ binding site has been underlined in all species and * denotes amino acids conserved in all species.

FIG. 4A shows the amino acid sequence alignment of cloned PCR products (without the primers) from asparagus (ASP, SEQ ID NO 2), Arabidopsis (ARA, SEQ ID NO 4), tobacco (TOB, SEQ ID NO 5), Brachypodium (ERA, SEQ ID NO 6) and wheat (WH and WHU, SEQ ID NOS 7 and 8). The * denote amino acids conerved in every species and denotes conservative amino acid changes.

FIG. 4B is the same as FIG. 4A but with the smaller wheat product removed to highlight sequence conservation between the other five PCR species.

FIGS. 5A–5C shows the SHH promoter sequence from Arabidopsis thaliana (SEQ ID NO 3) including the first 30 amino acids used in translational transgene fusions.

FIGS. 6A–6K comprise a map of the A. thaliana gene showing coding sequence, intron and 3' untranslated region. Important restriction sites are also shown.

FIGS. 7A–7D show the coversion of plasmid pSK AoPR1 FULL LUC via pSK AtSHH LUC to pBI101 At SHH Luc and pSK AtSHH-GUS to pBIN 19 AtSHH GUS and pBI101 At SHH Correct to pBI101 At SHH Wrong.

DETAILED DESCRIPTION OF THE INVENTION

EXAMPLE 1

Figure 7A:
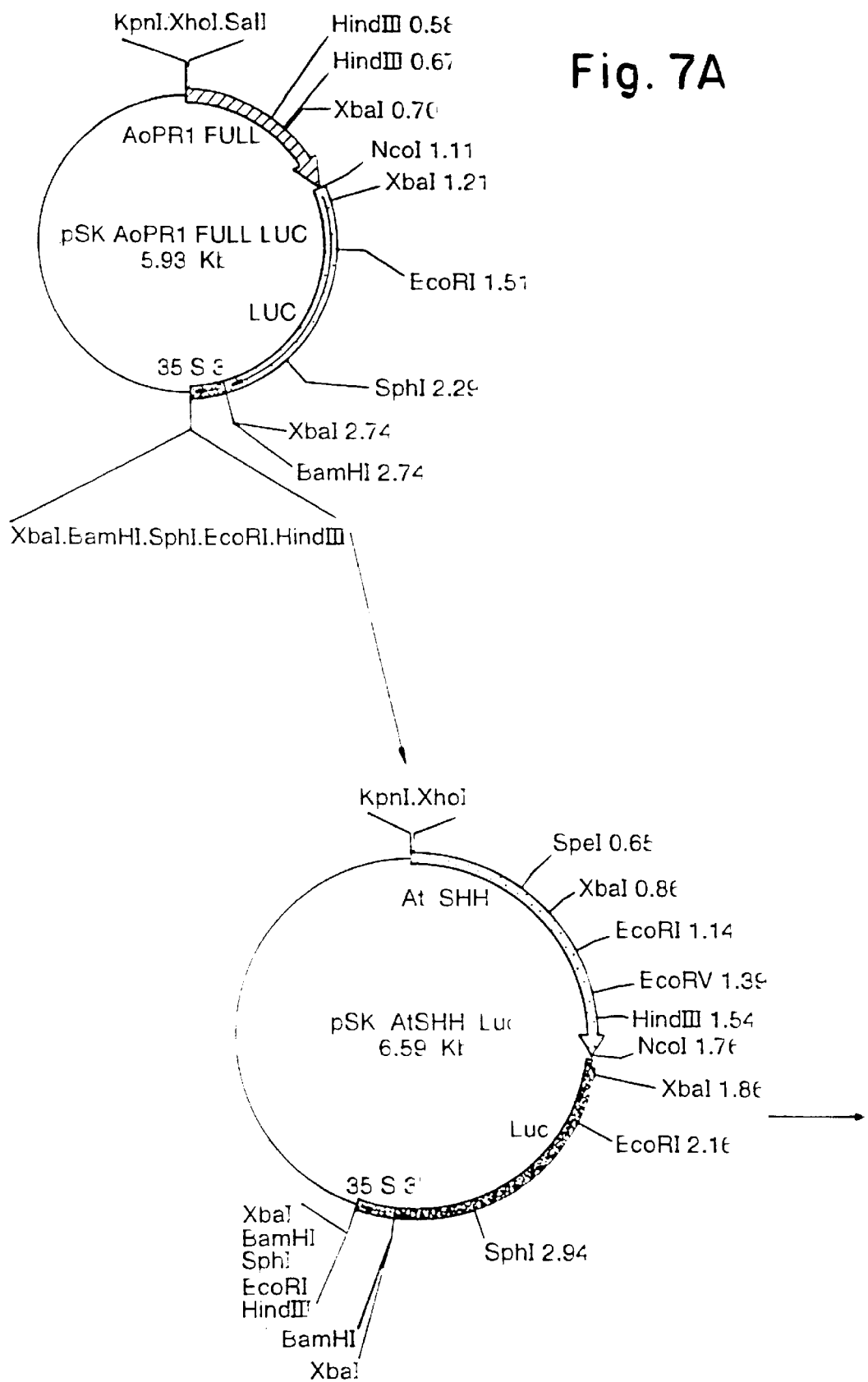

Elucidation of cDNA Sequence of Asparagus S-Adenosyl-L-Homocysteine Hydrolase

This research utilised previously constructed cDNA libraries derived from an mRNA population purified from mechanically separated Asparagus officinalis cells that had been prepared from asparagus seedlings by grinding in a mortar and pestle [Paul, E. et al. (1989), Plant Science, 65, 111–117 and Harikrishna, K., et.al. (1991), Journal of Experimental Botany, 42, 791–797].

Clones were randomly picked from the existing cDNA library made using mRNA extracted from model system cells 1–3 days after mechanical isolation and short stretches of derived sequence data. This data was analysed using Pearson and Lipman searches for homologous known sequences within the EMBL database. A putative asparagus SHH cDNA was identified in this manner and called DB6. This clone was subcloned and the full sequence was derived. The positions of the restriction sites used for this purpose are shown in FIGS. 1A–1F.

The nucleotide sequence itself and the translation of this deduced 1633 bp sequence were compared to the published SHH clones (particularly the parsley SHH), which demonstrated that DB6 was not full length, with 11 amino acids being absent from the amino terminus. Therefore existing libraries were rescreened using the DB6 insert as a probe and a full length version isolated (SEQ ID NO 1). Interestingly this version, named DBF, was isolated from a different library from the original clone. DB6 was picked from a day 1–3 library whereas DBF was isolated from a day 1 library. Sequence data revealed DBF to encode the full SHH amino acid sequence of 485 residues (SEQ ID NO 2), with 25 bp of 5' untranslated nucleotides, 284 bp of 3'-untranslated nucleotides and a polyA+ tail.

Genomic Southern data has shown that the asparagus SHH is probably a member of a small gene family, as was found with the parsley homolog. As with the parsley SHH, the asparagus SHH has been isolated from a model system. However, whereas a fungal elicitor was added to the cultured parsley cells, the asparagus system does not use elicitor treatment and relies on gene induction due to the mechanical isolation of the cells, and therefore it aims to isolate wound induced genes.

FIGS. 2A, 2B and 3A–3C show the asparagus SHH also contains the extra stretch of residues found in the photosynthetic species parsley and R. capsulatus and not in the other cloned SHH cDNAs from non-photosynthetic species. This 41 amino acid stretch, from 150–190 amino acids is as well conserved between the dicotyledon parsley and the monocotyledon asparagus as is the rest of the amino acid sequence, unlike the 36 residue stretch of R. capsulatus.

EXAMPLE 2

Isolation of SHH Genes from Other Plant Species and Demonstration of Sequence Conservation To enable further studies as to the significance of this 'extra' region in photosynthetic organisms amino acid sequence of SHH, PCR (Polymerase Chain Reaction) primers were designed to either side of the 41 amino acid stretch common to parsley and asparagus SHH. The primers designed were the following and are shown in context of the SHH cDNA in FIGS. 1A–1F:

PCR-1 (SEQ ID NO 10)

5' GCGTCTAGATGCAACATACTTCTCCAAC-CTAGGA 3'

PCR-2 (SEQ ID NO 11)

5' GCGTCTAGATTAGTCAAACTTGCTCTTG-GTAGAC 3'

It was expected that a PCR product of 482 bp would be produced in control experiments with asparagus genomic DNA as the template, unless an intron existed between the primer annealing sites in the genomic gene. The possibility of introns between the primer binding sites was ruled out following a PCR experiment showing that the expected 482 bp product was obtained. Of this 482 bp product, 63 bp consist of primer sequence (31 bp+32 bp). The first 9 bp of each primer, at the 5' end, were designed with an XbaI site to facilitate cloning of PCR products.

These PCR primers were used to try and amplify a segment of the SHH gene from several plant species whose DNA was available within the laboratory. For all species tested, similar sized products were obtained. When these products were hybridised to the asparagus SHH cDNA probe good hybridisation was observed. SHH PCR products were amplified from Arabidopsis, Asparagus (as a control), Tobacco, Brachypodium and Wheat. A single 480 bp PCR product was produced from the Arabidopsis, Asparagus and Brachypodium experiments; whereas wheat and tobacco both produced further products of 350 bp and 700 bp respectively, in addition to the predicted size product. In all cases a product of the predicted size was found. The second tobacco product of 700 bp was later proved to be this size due to multimers of PCR-2 primer sequence on one end, as a result of ligation or PCR error.

The other wheat product was smaller than predicted (350 bp) and when it was cloned and sequenced it was revealed why this was the case. Initial attempts to clone the PCR products into pBluescript (Trade Mark) using the XbaI site within the primers failed except for the control product from asparagus. Therefore a commercial vector available specifically for the cloning of PCR products was used, this vector is called PCRII. The vector utilises the fact that Taq polymerase used in PCR will add single deoxyadenosines to the 3'-end of all duplex molecules, therefore eliminating the need for restriction sites within the primers. All the PCR products from each species mentioned were cloned in this manner and then sequenced. This sequence data revealed why the initial attempts at cloning into pBluescript had failed. During the PCR reaction, for an unknown reason, the whole primer had not always been replicated at its 5'-end, causing the recognition site of XbaI not to be present in the final product. In most cases one primer had the site while the other did not.

All the clones were sequenced and multiple line-ups performed as can be seen in FIG. 4 which compares the deduced amino acid sequences for asparagus (SEQ ID NO 1), *A. thaliana* (SEQ ID NO 4), tobacco (SEQ ID NO 5), Brachypodium (SEQ ID NO 6) and the two wheat products (SEQ ID NOS 7 and 8). The smaller of the two wheat products proved to be more closely related to the nonphotosynthetic cDNAs isolated, in that it did not contain the extra stretch of 41 amino acids found in parsley and asparagus. The validity of this product needs to be checked as it may have arisen through contamination. Computer analysis has already proven this not to be the same as the Human SHH, previously cloned. However as a 480 bp wheat product was also cloned this could enhance the argument that SHH genes exist as small gene families encoding enzymes with differing biological/physiological roles.

In summary these data shows the SHH gene sequences to be highly conserved across the plant kingdom for the following reasons; firstly, the PCR primers facilitated the successful amplification of the SHH sequence from every tested plant species and secondly, the actual nucleotide and predicted amino acid sequence of this region shows how conserved the SHH gene is between plant species spanning the monocotyledon/dicotyledon classification. (See FIG. 4).

Thus it has been shown that the SHH amino acid sequence is highly conserved between a diverse range of plant species.

EXAMPLE 3

Demonstration of the Role of SHH in Transmethylation Reactions

Molecular and Biochemical Characterisation

It was predicted that an accumulation of SAH would inhibit the SAM mediated caffeic acid-O-methyltransferase reaction.

If, as suggested, SHH has a central role in allowing the transmethylation reactions of several metabolic pathways to occur unhindered it must be present and active in specific regions of the plant at specific developmental periods. Therefore the well studied lignification process occurring in the stems of maturing tobacco where two well characterised transmethylation reactions occur in the biosynthesis of lignin precursors would confirm the point. Although SHH transcript levels may vary between organs, for example lignifying stems, leaves, roots, pollen etc., it does not necessarily mean that the activity of the enzyme will be altered.

To examine the expression of the SHH gene in a range of tobacco organs, steady state mRNA levels were determined using northern analysis and enzyme assays were used to determine the level of enzyme activity.

Northerns were performed using standard techniques with the tobacco PCR product (FIG. 4) or cDNA as a hybridisation probe. Extraction of SHH enzyme and assay of activity were performed as follows:

All extraction steps were performed at 4° C.

1. Homogenise plant tissue (~1 g) by grinding in a pestle and mortar with 2 v/w extraction buffer [100 mM Tris pH8, 10 mM Sodium Metabisulphite, 10 mM Ascorbic Acid and 5 mM DTT added on day of use], acid washed sand and 0.1 g of insoluble PVP.
2. Decant the supernatant and centrifuge at 17000 g for 15 min. Remove the supernatant, noting the volume and add 0.56 g of solid ammonium sulphate per ml. Stir for 30 min.
3. Centrifuge at 17000 g for 15 min, resuspend the pellet in 2.5 ml of resuspension buffer [100 mM Tris pH8 and 5 mM DTT added on day of use] and clarify the solution by pulse centrifugation.
4. The extract is then desalted on a Pharmacia PD-10 G-25 column which has been pre-equilibrated with resuspension buffer according to the manufacturer's protocol. The resultant eluate is used in the following assay procedure.
5. Sequentially add the following to a microcentrifuge tube
   a) 10 µl of 100 mM DL-Homocysteine
   b) 80 µl of enzyme extract c) 10 μl of Adenosine (100 μl of 53 mCi/mmol $^{14}$C-adenosine and 100 μl of 20 mM adenosine)
6. Mix and incubate at 300° C. for 30 min.
7. Stop the reaction by adding 10 μl of 50% TCA and stand on ice for 10 min.
8. Centrifuge and apply 20 μl to a 1.5 cm wide strip on a silica TLC plate containing fluorescent indicator (F254, Merck). Develop the plate for a distance of 10 cm in butan-1-ol+acetic acid+water (12:3:5).
9. After allowing the plate to dry, visualise the SAH product with a UV lamp at 254 nm. Cut out these areas and elute the silica from the plate with 0.5 ml methanol before scintillation counting.

Northern analysis showed the SHH transcript to be detected at very low levels in most tissues tested. SHH enzyme assays demonstrated that transcript levels and enzyme activity levels do correlate strongly. Inducible SHH enzyme activity was found in wounded tissue from asparagus, tobacco and Arabidopsis when compared with SHH enzyme activity in unwounded tissue. The products of the enzyme assay were separated on a TLC plate according to Poulton and Butt (*Archives of Biochemistry and Biophysics* 172, 135–142, 1976) and both $^{14}$C labelled adenosine and S-adenosyl homocysteine were detected. The rf values of both $^{14}$C labelled compounds compared favourably with those obtained for unlabelled sources that were run on the plates simultaneously and detected by UV fluorescence. In the absence of homocysteine or enzyme preparation, no fluorescent products were observed with the same rf values as unlabelled SAH. These data demonstrate that $^{14}$C labelled SAH was derived from the catalytic conversion of $^{14}$C labelled adenosine and homocysteine by the SAH enzyme present in the plant preparations.

EXAMPLE 4

Isolation of a SHH Gene from *Arabidopsis thaliana*

The PCR fragment of the SHH gene from Arabidopsis was used to screen an Arabidopsis genomic library for the corresponding gene using standard techniques. Positive clones arising from the screen were analysed and the SHH gene sequenced from a candidate clone containing the gene and its promoter control regions. The DNA sequence of the promoter is shown in FIGS. 5A–5C and the DNA and deduced amino acid sequence of the coding region in FIGS. 6A–6K.

EXAMPLE 5

SHH Gene Down-Regulation and Over-Expression Studies

The Arabidopsis gene sequence described above was used in a series of experiments to modulate SHH gene activity either by down-regulation using antisense or partial sense constructs or by over-expression using the full coding sequence thus reducing the increasing SHH enzyme activity respectively. Effects in specific plant organs or at particular sites of metabolism may be achieved through use of appropriate gene promoters; for example, the lignification process may be modified by using a gene promoter isolated from a gene specific to lignifying tissues such as cinnamoyl:CoA reductase or cinnamyl alcohol dehydrogenase. Alternatively, specific organs may be targeted such as the anthers using the Arabidopsis A9 or APG promoters or pollen using the maize ZM13 promoter. Furthermore gene activity could be modified at sites of pathogen attack or wounding through use of wound promoter e.g. AoPRI from asparagus. Finally, SHH enzyme activities may be modified throughout the plant by using a promoter expressed in most plant tissues e.g. CaMV 35S.

EXAMPLE 6

Analysis of Arabidopsis SHH Promoter Activity

The promoter isolated from the Arabidopsis SHH gene has been tested in transgenic tobacco plants and in *A. thaliana* to establish its pattern of expression. As shown below this promoter has high level expression in all organs analysed and an additional activity which is induced following wounding. It therefore has utility as a constitutive promoter for expression of selectable markers for in vitro selection of transformants or for high level expression in mature plants. Furthermore, the wound induced activity may be used for directing gene products (e.g. antifungal proteins) to sites of wounding or pathogen invasion. Construction of the SHH promoter—reporter gene were undertaken as follows:

1. Transcriptional fusions between the SHH promoter and the luciferase (LUC) reporter gene.

The following construct is based on pSK AoPR1-LUC as described previously (Warner et al. The Plant Journal 6:31–43,1994). This construct (FIG. 7) was digested with NcoI and XhoI to remove the AoPRI promoter. Using these sites the Arabidopsis SHH promoter was ligated into the plasmid in front of Luc via an NcoI site to create pSK AtSHH-LUC (FIGS. 7A–7D), a cloning intermediate.

Figure 7B:
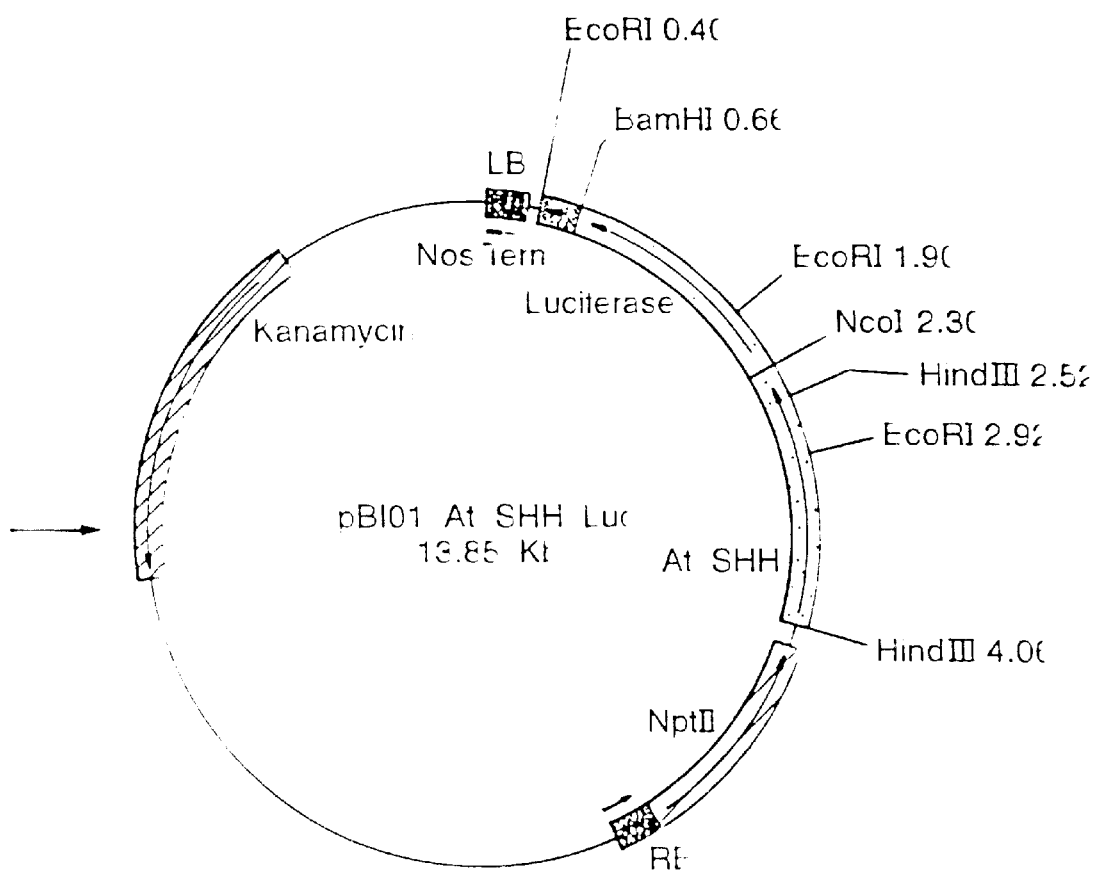
Figure 8:
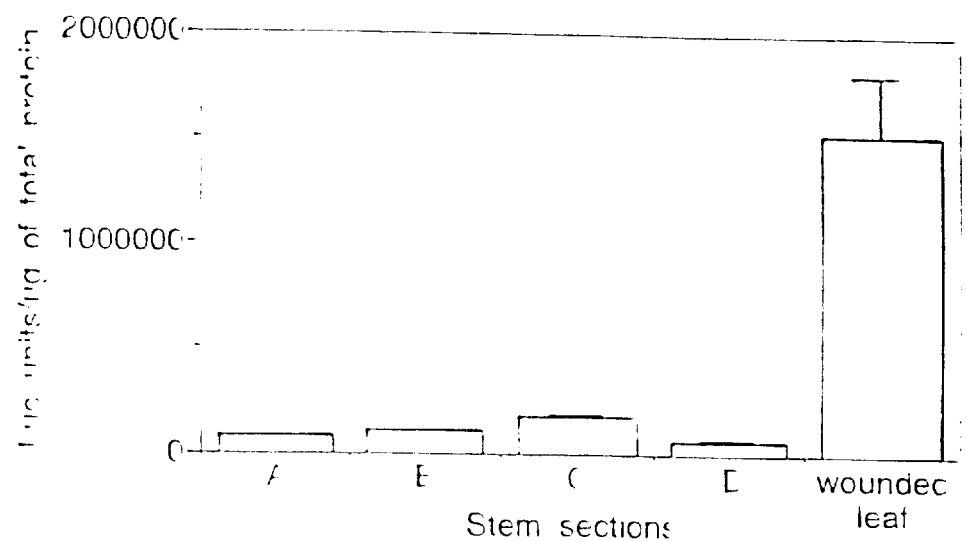
FIG. 8 shows a comparison of SHH driven LUC activity in stem sections and wounded leaf in tobacco.
Figure 9:
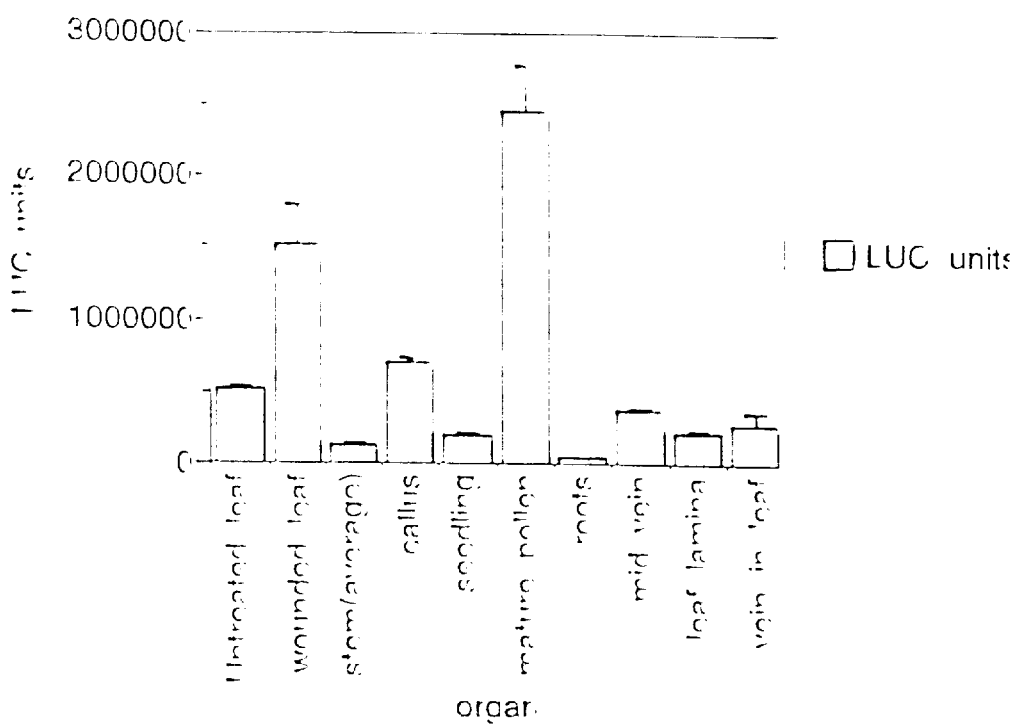
FIG. 9 shows SHH driven LUC expression in various tissues in tobacco.

The binary vector pBI01 AoPR1-LUC (Warner et al., 1994) was disgested with BamHI and SalI to remove the AoPRI-LUC cassette and the XhoI/BamHI-digested SHH promoter-LUC reporter cassette from pSK AtSHH-LUC (FIGS. 7A–7D) was ligated into the plasmid to create pBI01 AtSHH-LUC (FIG. 7B).

2. Transcriptional fusions between the SHH promoter and the glucuronidase (GUS) reporter gene.

Similar SHH promoter-reporter cassettes were constructed utilising the GUS reporter in place of the LUC reporter. This facilitated direct comparisons between the two reporters under the control of the same Arabidopsis SHH promoter.

Initially a pSK-derived plasmid containing a NOS terminator behind the GUS gene containing an NcoI site at the initiating methionine codon was digested with NcoI/XhoI. The Arabidopsis SHH promoter was similarly digested and ligated into the vector to create pSK AtSHH-GUS (FIG. 7C). The XhoI/BamHI fragment of this plasmid was then cloned into the BamHI/SalI sites of BIN19 (Bevan, M. (1984), *Nucleic Acids Research*, 12, 8711–8721) to create a binary plasmid pBIN19 AtSHH-GUS (FIG. 7C).

3. Translational fusions between the SHH promoter and the glucuronidase (GUS) reporter gene.

A simple one step cloning process allowed a further GUS fusion to be made using pBI01. From sequence data it was predicted that a fusion to be made using pBI01 would generate an active transitional fusion between the Arabidopsis SHH promoter and GUS with the first 30 amino acids of the GUS fusion encoded by the SHH gene. This construct was made by ligating the 1949 bp XhoI fragment of the SHH promoter into the SalI site of pBI01. The resultant clone was named pBI01.1 in the opposite orientation (i.e. in the antisense orientation) creating pBI01 AtSHH Wrong (FIG. 7D). This construct (FIG. 7D) was used as a negative control in expression studies.

REPORTER GENE ASSAYS

GUS activity was determined using standard techniques (Jefferson). LUC assays were performed essentially as in Ow et al. *Science,* 234, 856–859, 1986 with modifications described by Warner et al., 1994.

FIGS. 8–11 show luciferase activity data expressed as light units/µg total protein for one representative transgenic tobacco line. Identical reporter expression patterns were observed in several other SHH promoter-LUC and SHH promoter-GUS tobacco transgenic lines.

Figure 12:
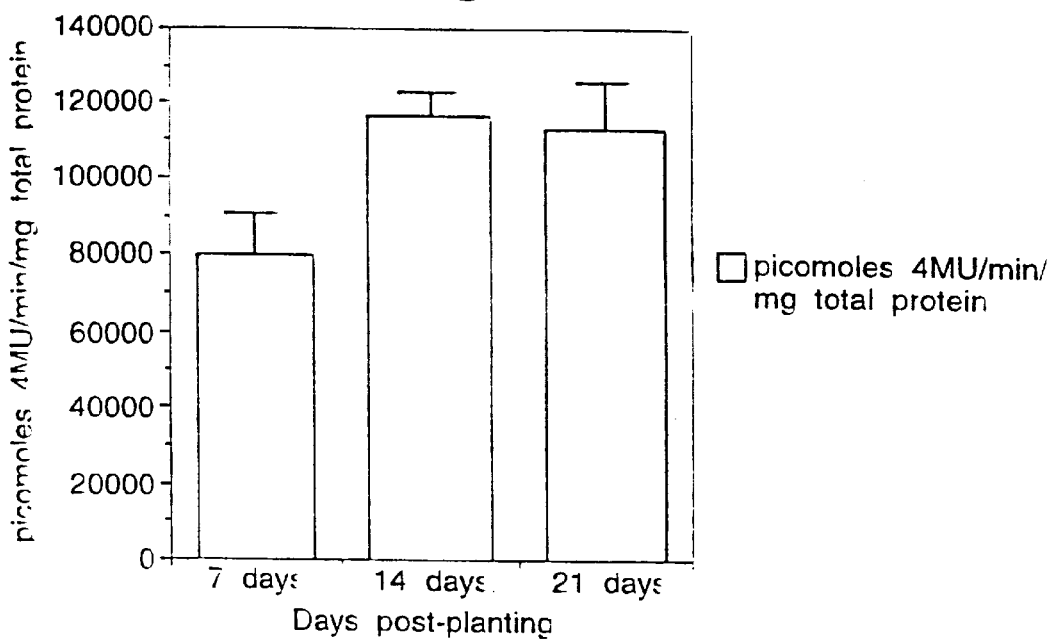
FIG. 12 shows SHH driven GUS expression during A. thaliana seedling development.
Figure 13:
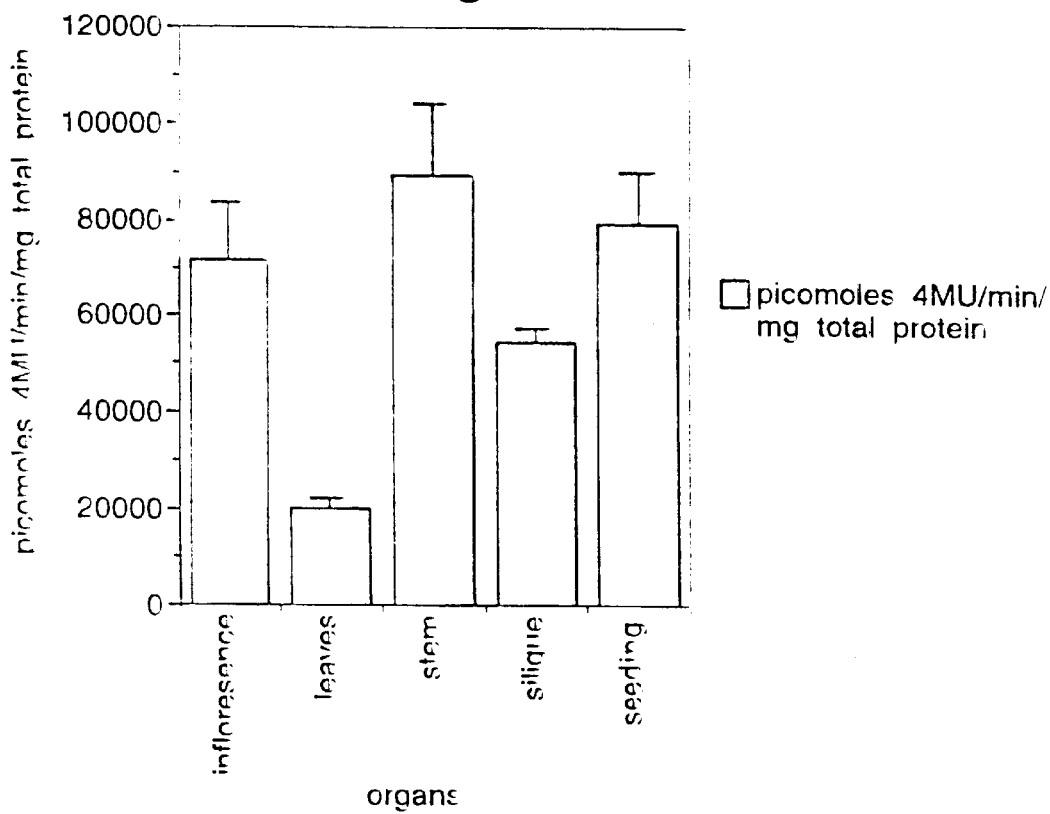
FIG. 13 shows SHH driven GUS expression in various A. thaliana tissues.

Similar patterns of reporter gene expression were also observed within transgenic *A. thaliana,* as demonstrated in FIGS. 12 and 13. These *A. thaliana* transgenics represent T3 homozygous lines containing a single copy T-DNA. Fluorometric assays of GUS activity within leaves of several fo these lines prove that the exprssion due to the SHH promoter occurs at levels similar to or greater than CaMV35s-driven GUS levels in similar transformants. Of seventy-one individual transformed lines harbouring the pBI121 [Jefferson et al (1987) *EMBO J.,* 6, 3901–3907], the highest activity within leaves was found to be 12040 pmol MU/min/mg, with an average between 2000 and 3000 pmol MU/min/mg [Clarke et al, (1992) *Plant Mol. Biol. Reporter,* 10, 178–189]. Of the five chosen SHH-GUS *A. thaliana* homozygous T3 lines, the expression within leaves varies from 20984 pmol MU/min/mg to 4420 pmol MU/min/mg with an average of 13725 pmol MU/min/mg, a greater value than the highest expressing line using pBI121.

Histochemically stained transgenic tobacco tissues supported the expression data for GUS activity in all tissues tested.

These results show that the AtSHH promoter drives reporter gene expression in all tissues tested. The point of interest lies in the respective levels of the expression. AtSHH promoter reporter gene expression levels in transgenic plants were far higher than would be predicted from the levels of endogenous SHH transcript. The results in tobacco may be explainable in terms of aberrant expression driven by the Arabidopsis promoter in the tobacco host plant due to incorrect transcription factors recognising the introduced promoter but the increased levels of expression in *A. thaliana* suggest that this is not the case. Alternatively, the high levels of reporter gene activity could be a result of stabilisation or high levels of translation of the reporter gene transcript affected by the Arabidopsis SHH 5' leader sequence present in all constructs made.

The AtSHH promoter, has been demonstrated to cause increased reporter gene expression in tobacco and in *A. thaliana,* and this demonstrates its utility as a high level constitutive promoter.

Figure 10:
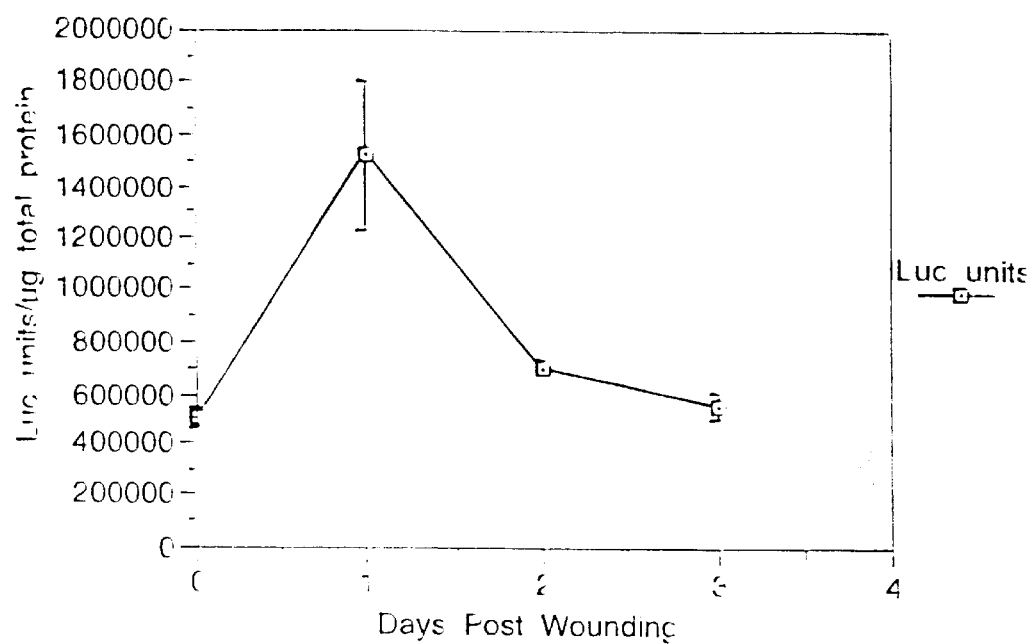
FIG. 10 shows LUC line 11 wounding time course in tobacco.
Figure 11:
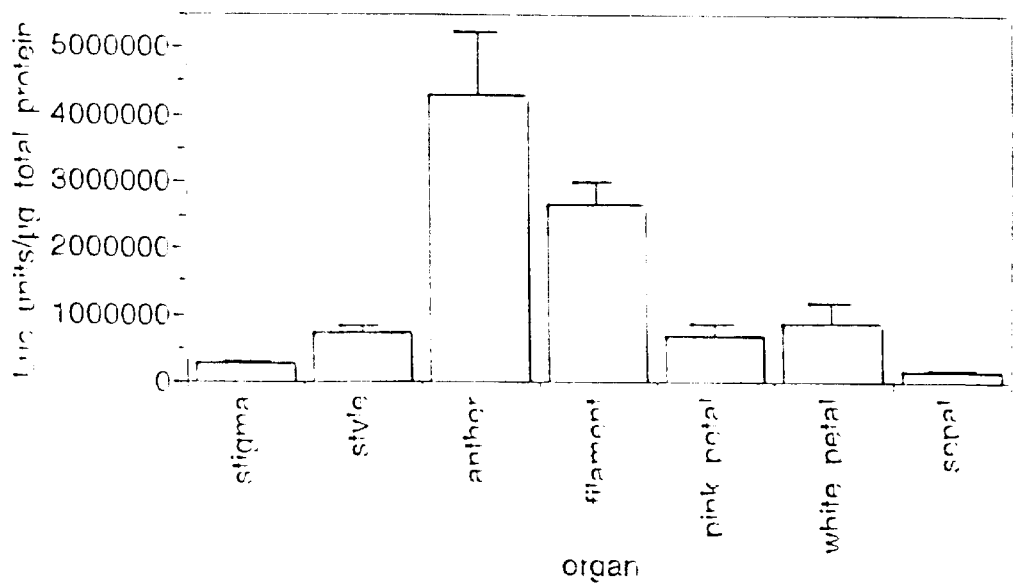
FIG. 11 shows LUC line 11; open flower non dehisced in tobacco.

Furthermore, superimposed on the constitutive expression pattern of the AtSHH promoter is a 2.5-fold increase in expression at wound sites which can be clearly seen in FIG. 10.

EXAMPLE 7

To establish utility of the Arabidopsis SHH promoter in directing expression of an ATP gene and providing resistance to a fungal pathogen, the 1760 bp promoter fragment from pSKAt SHH-GUS was amplified by PCR using the primers to change the 5' XhoI site to HindIII and the NcoI site at the ATG start codon to XhoI. The resulting fragment was cloned directly into a pMJB1 vector as a partial HindIII-XhoI fragment such that the promoter is placed upstream of the ATP gene. An omega translational enhancer from tobacco mosaic virus, located between the SHH promoter and the ATP gene is included to increase the level of gene expression. In this example, the ATP gene is Dm-AMP1 obtained from seeds of *Dahlia merckii*. The resulting construct was introduced into oilseed rape using standard Agrobacterium-mediated transformation techniques. Transformed plants wre screened for expression of the Dm-AMP1 gene using western blotting techniques and expressing lines advanced into detached leaf disease assays with the oil seed rape pathogen *Phoma lingam* (Gretenkort and Ingram (1993), *J. Phytopathology,* 137, 89–104). Introduction of the Dm-AMP1 gene and expression by the SHH promoter resulted in increased resistance to infection by *Phoma lingam*. These observations parallel those obtained when expression of the Dm-AMP1 gene is controlled by a well-known constitutive promoter, 35S, from cauliflower mosaic virus, exemplifying the utility of the SHH promoter in this application.

```
                       SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 1767 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: SHH GENE FROM ASPARAGUS (ix) FEATURE:
         (A) NAME/KEY: CDS
```

(B) LOCATION:26..1483
(D) OTHER INFORMATION:/codon_start= 26
    /product= "Asparagus SHH"

(xi) SEQUENCE DESCRIPTION: SEQ ID NO: 1:

```
CTCGTTTCAG ATCCGATCTG AAGAA ATG GCT CTC CTC GTT GAG AAG ACT ACC        52
                            Met Ala Leu Leu Val Glu Lys Thr Thr
                             1               5

TCT GGC CGC GAG TAC AAG GTC AAG GAC ATG TCT CAG GCC GAC TTC GGC       100
Ser Gly Arg Glu Tyr Lys Val Lys Asp Met Ser Gln Ala Asp Phe Gly
 10              15                  20                  25

CGC CTC GAG ATC GAG CTC GCT GAG GTC GAG ATG CCA GGG CTC ATG GCC       148
Arg Leu Glu Ile Glu Leu Ala Glu Val Glu Met Pro Gly Leu Met Ala
                 30                  35                  40

TGC CGT GCC GAG TTC GGC CCC GCC CAG CCA TTC AAG GGC GCA AAA ATC       196
Cys Arg Ala Glu Phe Gly Pro Ala Gln Pro Phe Lys Gly Ala Lys Ile
             45                  50                  55

ACT GGA TCC CTC CAC ATG ACG ATC CAA ACT GCC GTC CTC ATC GAA ACC       244
Thr Gly Ser Leu His Met Thr Ile Gln Thr Ala Val Leu Ile Glu Thr
         60                  65                  70

CTA ACC GCC CTC GGG CCC GAG GTT CGC TGG TGC TCC TGC AAC ATA TTC       292
Leu Thr Ala Leu Gly Pro Glu Val Arg Trp Cys Ser Cys Asn Ile Phe
     75                  80                  85

TCC ACC CAG GAC CAT GCC GCC GCT GCC ATT GCC CGT GAC TCC GCC TCC       340
Ser Thr Gln Asp His Ala Ala Ala Ala Ile Ala Arg Asp Ser Ala Ser
 90                  95                 100                 105

GTC TTC GCC TGG AAG GGT GAG ACC CTC CAG GAG TAC TGG TGG TGC ACC       388
Val Phe Ala Trp Lys Gly Glu Thr Leu Gln Glu Tyr Trp Trp Cys Thr
                110                 115                 120

GAG CGT GCC CTC GAC TGG GGC CCC GGC GGT GGC CCT GAC CTC ATC GTC       436
Glu Arg Ala Leu Asp Trp Gly Pro Gly Gly Gly Pro Asp Leu Ile Val
            125                 130                 135

GAT GAC GGC GGC GAC ACC ACT CTC TTG ATC CAT GAG GGG GTG AAG GCC       484
Asp Asp Gly Gly Asp Thr Thr Leu Leu Ile His Glu Gly Val Lys Ala
        140                 145                 150

GAG GAA GAG TAC GAG AAG ACG GGG AAG ATG CCC GAT CCG GCG TCT ACC       532
Glu Glu Glu Tyr Glu Lys Thr Gly Lys Met Pro Asp Pro Ala Ser Thr
    155                 160                 165

GAC AAT GCT GAG TTC CAG ATC GTG CTC ACA ATC ATC AGG GAT GGG CTC       580
Asp Asn Ala Glu Phe Gln Ile Val Leu Thr Ile Ile Arg Asp Gly Leu
170                 175                 180                 185

AAG GTG GAC CCC ACC AAG TAC AGG AAG ATG AAG GAT AGG ATT GTC GGT       628
Lys Val Asp Pro Thr Lys Tyr Arg Lys Met Lys Asp Arg Ile Val Gly
                190                 195                 200

GTG TCG GAG GAG ACC ACC ACC GGG GTC AAG AGG CTT TAC CAG ATG CAG       676
Val Ser Glu Glu Thr Thr Thr Gly Val Lys Arg Leu Tyr Gln Met Gln
            205                 210                 215

GCT AAC AAT TCC CTT CTT TTC CCT GCG ATC AAT GTC AAT GAC TCC GTC       724
Ala Asn Asn Ser Leu Leu Phe Pro Ala Ile Asn Val Asn Asp Ser Val
        220                 225                 230

ACC AAG AGC AAG TTT GAC AAT CTG TAT GGA TGC CGG CAC TCT CTT CCC       772
Thr Lys Ser Lys Phe Asp Asn Leu Tyr Gly Cys Arg His Ser Leu Pro
    235                 240                 245

GAT GGT CTG ATG AGG GCC ACT GAT GTT ATG ATT GCT GGC AAG GTT GCA       820
Asp Gly Leu Met Arg Ala Thr Asp Val Met Ile Ala Gly Lys Val Ala
250                 255                 260                 265

GTT GTC TGC GGT TAT GGT GAT GTC GGA GAG GGC TGT GCT GCT GCA CTC       868
Val Val Cys Gly Tyr Gly Asp Val Gly Glu Gly Cys Ala Ala Ala Leu
                270                 275                 280

AAG CAG GCT GGT GCC CGT GTT ATT GTG ACG GAG ATC GAC CCC ATC TGT       916
```

```
                                                                  Lys Gln Ala Gly Ala Arg Val Ile Val Thr Glu Ile Asp Pro Ile Cys
                                                                              285                 290                 295

GCT CTT CAA GCC CTA ATG GAG GGT CTT CAG GTC CTC ACC CTC GAG GAT       964
Ala Leu Gln Ala Leu Met Glu Gly Leu Gln Val Leu Thr Leu Glu Asp
            300                 305                 310

GTT GTC TCA GAG GCG GAT ATC TTT GTT ACC ACC ACC GGT AAC AAG GAC      1012
Val Val Ser Glu Ala Asp Ile Phe Val Thr Thr Thr Gly Asn Lys Asp
        315                 320                 325

ATC ATC ATG CTG GAC CAC ATG AGG AAG ATG AAG AAC AAT GCC ATT GTC      1060
Ile Ile Met Leu Asp His Met Arg Lys Met Lys Asn Asn Ala Ile Val
330                 335                 340                 345

TGC AAC ATT GGT CAC TTT GAC AAC GAG ATT GAC ATG CTA GGT TTG GAG      1108
Cys Asn Ile Gly His Phe Asp Asn Glu Ile Asp Met Leu Gly Leu Glu
                350                 355                 360

ACA TAC CCT GGC ATC AAG AGA ATC ACC ATC AAG CCC CAG ACT GAC CGG      1156
Thr Tyr Pro Gly Ile Lys Arg Ile Thr Ile Lys Pro Gln Thr Asp Arg
            365                 370                 375

TGG GTC TTC CCT GAA ACC AAC ACT GGT ATA ATT GTT CTT GCT GAG GGC      1204
Trp Val Phe Pro Glu Thr Asn Thr Gly Ile Ile Val Leu Ala Glu Gly
        380                 385                 390

CGA CTC ATG AAC CTT GGG TGT GCC ACT GGT CAC CCC AGC TTT GTC ATG      1252
Arg Leu Met Asn Leu Gly Cys Ala Thr Gly His Pro Ser Phe Val Met
395                 400                 405

TCC TGC TCC TTC ACC AAC CAG GTG ATT GCT CAG CTA GAG TTG TGG AAT      1300
Ser Cys Ser Phe Thr Asn Gln Val Ile Ala Gln Leu Glu Leu Trp Asn
410                 415                 420                 425

GAG AAG GCA AGC GGC AAG TAT GAG AAG AAG GTT TAC GTG CTC CCC AAG      1348
Glu Lys Ala Ser Gly Lys Tyr Glu Lys Lys Val Tyr Val Leu Pro Lys
                430                 435                 440

CAT CTT GAT GAG AAA GTA GCA GCG CTT CAC TTG GGC AAG CTC GGA GCC      1396
His Leu Asp Glu Lys Val Ala Ala Leu His Leu Gly Lys Leu Gly Ala
            445                 450                 455

AAG CTT ACA AAG CTC AGC CCT TCA CAG GCG GAC TAC ATC AGC GTC CCC      1444
Lys Leu Thr Lys Leu Ser Pro Ser Gln Ala Asp Tyr Ile Ser Val Pro
        460                 465                 470

ATC GAG GGT CCC TAC AAG CCA CCT CAC TAC AGG TAC TAG ACGCTGTTGT       1493
Ile Glu Gly Pro Tyr Lys Pro Pro His Tyr Arg Tyr *
475                 480                 485

GCCGGGGAGA GATCATCGCA GCAAGAAAGT ATTAAGATTG AAGAAGAGAG TTGTTATGGA    1553

GGACATGGCT ATATTTACTT TATTTCCTAC CTATTTCTTG CTGTTTCTCT TTCCGAACTT    1613

TTAGACTGAT CCTCTTCTTC TCTTTGATTT ATTACGATAT GAATTCTGTT TAAATTTTGC    1673

TTATTCTCTA ATGATGAGCT AGCAGACATA TGTTCTGTGG TAGAATAACG AGGTTTTGAA    1733

CTTTGTGCAA AAAAAAAAAA AAAAAAAAAA AAAA                                1767

(2) INFORMATION FOR SEQ ID NO: 2:

(i) SEQUENCE CHARACTERISTICS:
        (A) LENGTH:   485 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Leu Leu Val Glu Lys Thr Thr Ser Gly Arg Glu Tyr Lys Val
  1               5                  10                  15

Lys Asp Met Ser Gln Ala Asp Phe Gly Arg Leu Glu Ile Glu Leu Ala
            20                  25                  30
```

-continued

```
Glu Val Glu Met Pro Gly Leu Met Ala Cys Arg Ala Glu Phe Gly Pro
             35                  40                  45

Ala Gln Pro Phe Lys Gly Ala Lys Ile Thr Gly Ser Leu His Met Thr
         50                  55                  60

Ile Gln Thr Ala Val Leu Ile Glu Thr Leu Thr Ala Leu Gly Pro Glu
 65                  70                  75                  80

Val Arg Trp Cys Ser Cys Asn Ile Phe Ser Thr Gln Asp His Ala Ala
                 85                  90                  95

Ala Ala Ile Ala Arg Asp Ser Ala Ser Val Phe Ala Trp Lys Gly Glu
                100                 105                 110

Thr Leu Gln Glu Tyr Trp Trp Cys Thr Glu Arg Ala Leu Asp Trp Gly
            115                 120                 125

Pro Gly Gly Pro Asp Leu Ile Val Asp Asp Gly Asp Thr Thr
        130                 135                 140

Leu Leu Ile His Glu Gly Val Lys Ala Glu Glu Tyr Glu Lys Thr
145                 150                 155                 160

Gly Lys Met Pro Asp Pro Ala Ser Thr Asp Asn Ala Glu Phe Gln Ile
                165                 170                 175

Val Leu Thr Ile Ile Arg Asp Gly Leu Lys Val Asp Pro Thr Lys Tyr
                180                 185                 190

Arg Lys Met Lys Asp Arg Ile Val Gly Val Ser Glu Glu Thr Thr Thr
            195                 200                 205

Gly Val Lys Arg Leu Tyr Gln Met Gln Ala Asn Asn Ser Leu Leu Phe
        210                 215                 220

Pro Ala Ile Asn Val Asn Asp Ser Val Thr Lys Ser Lys Phe Asp Asn
225                 230                 235                 240

Leu Tyr Gly Cys Arg His Ser Leu Pro Asp Gly Leu Met Arg Ala Thr
                245                 250                 255

Asp Val Met Ile Ala Gly Lys Val Ala Val Val Cys Gly Tyr Gly Asp
                260                 265                 270

Val Gly Glu Gly Cys Ala Ala Ala Leu Lys Gln Ala Gly Ala Arg Val
        275                 280                 285

Ile Val Thr Glu Ile Asp Pro Ile Cys Ala Leu Gln Ala Leu Met Glu
        290                 295                 300

Gly Leu Gln Val Leu Thr Leu Glu Asp Val Val Ser Glu Ala Asp Ile
305                 310                 315                 320

Phe Val Thr Thr Thr Gly Asn Lys Asp Ile Ile Met Leu Asp His Met
                325                 330                 335

Arg Lys Met Lys Asn Asn Ala Ile Val Cys Asn Ile Gly His Phe Asp
            340                 345                 350

Asn Glu Ile Asp Met Leu Gly Leu Glu Thr Tyr Pro Gly Ile Lys Arg
            355                 360                 365

Ile Thr Ile Lys Pro Gln Thr Asp Arg Trp Val Phe Pro Glu Thr Asn
        370                 375                 380

Thr Gly Ile Ile Val Leu Ala Glu Gly Arg Leu Met Asn Leu Gly Cys
385                 390                 395                 400

Ala Thr Gly His Pro Ser Phe Val Met Ser Cys Ser Phe Thr Asn Gln
                405                 410                 415

Val Ile Ala Gln Leu Glu Leu Trp Asn Glu Lys Ala Ser Gly Lys Tyr
            420                 425                 430

Glu Lys Lys Val Tyr Val Leu Pro Lys His Leu Asp Glu Lys Val Ala
        435                 440                 445

Ala Leu His Leu Gly Lys Leu Gly Ala Lys Leu Thr Lys Leu Ser Pro
```

```
                450             455              460
Ser Gln Ala Asp Tyr Ile Ser Val Pro Ile Glu Gly Pro Tyr Lys Pro
465                 470              475                  480

Pro His Tyr Arg Tyr
            485
```

(2) INFORMATION FOR SEQ ID NO: 3:

(i) SEQUENCE CHARACTERISTICS:
        (A) LENGTH: 1847 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

```
CTCGAGTGTT GACCTTTTCT GGTCGATTGA ATAGAATCGA ATGTCTTAAT CCAGTACCCT    60

CCAGCTTTTA TTTCGTGTAA TTTATTTTCC AAACCTACCA CTACCAGTTT CATAACTCTC   120

GAATAAATTT ATCAAATAGT CTTTTGAGTG CTCAAAGTCT TGGGATAATA AATGGTCAGT   180

GCTATGTATC ACCCGGATGT GAAACATTAT GGGTGGAGAT AGACTATTAT AAATTTATTG   240

AAATATACGA TTGTTACTCG TTTAATAGCA AAAGTAGTAC AATGTATATA GTTTCTATCG   300

AGAACAAGAT CTATTTAAAA TTCGAAAAGT ACATTTAAAA TTCATAAACA TATAAAGATA   360

GTAACATGTT AGATCTGCAT AGTACCACCA AAACAAGAAA AAAGAAACGC ACATCGCCAC   420

ATAATTGCTA TGATTCTCAC TGTCGGCTGC TTTGAAATAT TCGATTCTTT TGGTAAATCA   480

CACAACATAA TATAATTACA ATAAATATAT ATATACTAAA GTATAATTAA TATAATTAAT   540

ACCACATTGT TTAATTCTGT TTTGATCTTT TAAGATCAGT CAGATCCACC GACGTTCCTA   600

CACGCGCAGG TCCAGATCCA AACAGCACAC ACACACACAC AATGCCACTA GTGTAAATGC   660

TTGGTGGCTA TTGCATTTGC ACCTATTGAT ACTCTTTCTT CAAAAACAAG TTATTGTTTT   720

TATTTTCAAC CCAACTTTAA TACGGATTCA TACTGGGATT TAGGTGTTAA ATCTGATAAT   780

TTAGGTTTGA ATAAGTTGTA TATTTGTTTC TTTGATTAAA AAAAGAACCT ATATATATAC   840

AAAAATAAAT AAAAAGTTCT AGATTTCAAT TTTCCGTATA TAGCGGGTTG AATTGTCTAT   900

TTTAATATGA AAATTGCGGA TCTTATAAAC AAAATGTTCT GAAATATGTA AAAGGATTTA   960

GCCAAAGTTA ACCAAAAAAA AAAAAACAAA CAGAAAAGTC ACATTCACAT GTCGTGGTAG  1020

ATCTAAGGCA TTAATTTAGA AATATGTCGT TACAATAAGC GGAGAACATG GGACGTTTCT  1080

CGTGGTCCAA TCAGACGAAC GAGATCTCAT AAATTAAATG ACTTCAGCGA GGGAATTCAT  1140

GGCAGAATGA TAATGCAACT TAAGTGACTT TAGAGTGAAA ATGATACGAG AACAATGCAT  1200

AATCCATATG ACCGTTGAGT GAGTGATACC ATTAGCGCGA TACAAGCGGG ACTATAAACT  1260

GATCTAGATT GTTTTTCTTG GGAAAAAATG TTACAAATTT TAAATATGTA GTTTGAATTG  1320

TTAAACCAAG ATTCAACAGA AATATACCGT AAATAAACAA CAGTTGATAA TAGTCATCGA  1380

AAAGATATCA ACTGATTCTT CACTTGGGCT ACTGTGACGG CCCGTTAGGT TCTCAATATA  1440

AGTCAATAAC TACGATCTAC GATTCACTGA AACAAATAAA ACACAGCCAC GTGTCCACCC  1500

TCCCACATCA CCGTCCGATC TAACCCACGA CAAGCTTACA CACGGGTCA TACCGGCTCG  1560

TGCAGCGTGT TCCGTCATCC ACGGGATTAC AACTTCTACC AGATCCACCA AACCCTCAAA  1620

ACAATCTGAA CCGTTCATTT CATTTTGACC TCATCTATAT ATTCTCTGTC ACTCCCCTTT  1680

CTCTTCTCCT CGCACACACT TCTCTCTCTC TCTCTCTCTG CCTCCTTTCG GATTCAAATC  1740
```

TCAGATCTAG CTCAACCATG GCGTTGCTCG TCGAGAAGAC CTCAAGTGGC CGTGAATACA    1800

AGGTCAAAGA CATGTCTCAA GCCGATTTCG GTCGTCTCGA ACTCGAG    1847

(2) INFORMATION FOR SEQ ID NO: 4:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: ARABIDOPSIS SHH PROTEIN (xi) SEQUENCE DESCRIPTION: SEQ ID NO: 4:

His Ala Ala Ala Ile Ala Arg Asp Ser Ala Ala Val Phe Ala Trp
1               5                   10                  15

Lys Gly Glu Thr Leu Gln Glu Tyr Trp Trp Cys Thr Glu Arg Ala Leu
            20                  25                  30

Asp Trp Gly Pro Gly Gly Pro Asp Leu Ile Val Asp Asp Gly Gly
        35                  40                  45

Asp Ala Thr Leu Phe Arg Ile His Glu Gly Val Lys Ala Glu Glu Ile
    50                  55                  60

Phe Glu Lys Thr Gly Gln Val Pro Asp Pro Thr Ser Thr Asp Asn Pro
65                  70                  75                  80

Glu Phe Gln Ile Val Leu Ser Ile Ile Lys Glu Gly Leu Gln Val Asp
                85                  90                  95

Pro Arg Lys Tyr His Lys Met Lys Glu Arg Leu Val Gly Val Ser Glu
                100                 105                 110

Glu Thr Thr Thr Gly Val Lys Arg Leu Tyr Gln Met Gln Glu Asn Gly
            115                 120                 125

Thr Leu Leu Phe Pro Ala Ile Asn Val Asn Asp Ser
        130                 135                 140

(2) INFORMATION FOR SEQ ID NO: 5:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: TOBACCO SHH PROTEIN (xi) SEQUENCE DESCRIPTION: SEQ ID NO: 5:

His Ala Ala Ala Ile Ala Arg Asp Ser Arg Ala Val Phe Ala Trp
1               5                   10                  15

Lys Gly Glu Thr Leu Gln Glu Tyr Trp Trp Cys Thr Glu Arg Ala Leu
            20                  25                  30

Asp Trp Gly Pro Gly Gly Gly Pro Asp Leu Ile Val Asp Asp Gly Gly
        35                  40                  45

Asp Ala Thr Leu Leu Ile His Glu Gly Val Lys Ala Glu Glu Glu Tyr
    50                  55                  60

Ala Lys Ser Gly Lys Leu Pro Asp Pro Ser Ser Thr Asp Asn Val Glu
65                  70                  75                  80

Phe Gln Leu Val Thr Ile Ile Arg Asp Gly Leu Lys Thr Asp Pro Leu

```
                    85                  90                  95
Lys Tyr Thr Glu Met Lys Glu Arg Leu Val Gly Val Ser Glu Glu Thr
                100                 105                 110

Thr Thr Gly Val Lys Arg Leu Tyr Gln Met Gln Ala Asn Gly Thr Leu
        115                 120                 125

Leu Phe Pro Ala Ile Asn Val Asn Asp Ser
    130                 135

(2) INFORMATION FOR SEQ ID NO: 6:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BRACHYPODIUM SHH PROTEIN (xi) SEQUENCE DESCRIPTION: SEQ ID NO: 6:

His Ala Ala Ala Ala Ile Ala Arg Asp Ser Ala Ala Val Phe Ala Trp
1               5                   10                  15

Lys Gly Glu Thr Leu Glu Glu Tyr Trp Trp Cys Thr Glu Arg Cys Leu
            20                  25                  30

Asp Trp Gly Val Gly Gly Pro Asp Leu Ile Val Asp Asp Gly Gly
        35                  40                  45

Asp Pro Thr Leu Leu Ile His Glu Gly Val Lys Ala Glu Glu Phe
    50                  55                  60

Glu Lys Ser Gly Lys Ile Pro Asp Pro Glu Ser Ala Asp Asn Pro Glu
65                  70                  75                  80

Phe Lys Ile Val Leu Thr Ile Ile Arg Asp Gly Leu Lys Thr Asp Ala
                85                  90                  95

Arg Lys Tyr Arg Lys Met Lys Glu Arg Leu Val Gly Val Ser Glu Glu
                100                 105                 110

Thr Thr Thr Gly Ala Lys Arg Leu Tyr Gln Thr Gln Asn Pro Gly Thr
        115                 120                 125

Leu Leu Phe Pro Ala Ile Asn Val Asn Asp Ser
    130                 135

(2) INFORMATION FOR SEQ ID NO: 7:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: WHEAT SHH PROTEIN (1)

(xi) SEQUENCE DESCRIPTION: SEQ ID NO: 7:

Arg Ala Ala Ala Ala Ile Ala Arg Asp Ser Ala Ser Val Phe Ala Trp
1               5                   10                  15

Lys Gly Glu Thr Leu Gln Gly Tyr Trp Trp Cys Thr Glu Arg Ala Leu
            20                  25                  30

Asp Trp Gly Pro Gly Gly Gly Leu Asp Leu Ile Val Asp Asp Gly Gly
        35                  40                  45
```

Asp Thr Thr Leu Leu Ile His Glu Gly Val Lys Ala Glu Glu Glu Tyr
50                      55                      60

Glu Lys Thr Gly Lys Met Pro Asp Pro Thr Ser Thr Asp Asn Ala Glu
65                      70                      75                      80

Phe Gln Ile Val Leu Thr Ile Ile Arg Asp Gly Leu Lys Val Asp Pro
                  85                      90                      95

Thr Lys Tyr Arg Lys Met Lys Asp Arg Ile Val Gly Val Ser Glu Glu
                100                     105                     110

Thr Thr Thr Gly Val Lys Arg Leu Tyr Gln Met Gln Ala Asn Asn Ser
                115                     120                     125

Leu Leu Phe Leu Thr Ile Asn Val Asn Asp Ser
130                     135

(2) INFORMATION FOR SEQ ID NO: 8:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: WHEAT SHH PROTEIN (2)

(xi) SEQUENCE DESCRIPTION: SEQ ID NO: 8:

Gln Ala Ala Ala Ile Ala Ala Gly Ile Pro Val Phe Ala Trp
1                 5                      10                      15

Lys Gly Glu Thr Glu Glu Tyr Glu Trp Cys Ile Glu Gln Thr Ile
                  20                      25                      30

Leu Lys Asp Gly Lys Pro Trp Asp Ala Asn Met Val Leu Asp Asp Gly
                  35                      40                      45

Gly Asp Leu Thr Glu Ile Leu His Lys Lys Tyr Pro Gln Met Leu Glu
50                      55                      60

Arg Ile His Gly Ile Thr Glu Glu Thr Thr Thr Gly Val His Arg Leu
65                      70                      75                      80

Leu Asp Met Leu Lys Ala Gly Thr Leu Lys Val Pro Ala Ile Asn Val
                  85                      90                      95

Asn Asn Ala (2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

GCGTCTAGAT GCAACATMTT CTCMACYCAG GA                                32

(2) INFORMATION FOR SEQ ID NO: 10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA -continued (xi) SEQUENCE DESCRIPTION: SEQ ID NO: 10:

GCGTCTAGAT TRTCAAACTT GCTCTTGGTR AC    32

We claim:

1. An isolated promoter derived from the S-adenosyl-L-homocysteine hydrolase gene of *A. thaliana*.

2. An isolated promoter having the nucleotide sequence of that part of SEQ ID NO 3 which is upstream of the methionine codon as shown in FIGS. 5A–5C.

3. A DNA construct comprising a promoter as claimed in claim 1 or claim 2 operably linked to a gene.

4. A DNA construct as claimed in claim 3 wherein said gene is selected from the group consisting of a gene encoding S-adenosyl-L-homocysteine hydrolase, an antifungal protein gene, a selectable marker gene, NptII, a kanamycin resistance gene, a phosphinothricin resistance gene, the phosphinothricin acetyl transferase (PAT) gene, the glucuronidase (GUS) reporter gene, and the luciferase (LUC) reporter gene.

5. A vector comprising a DNA construct as claimed in claim 3 or claim 4.

6. A vector as claimed in claim 5 which is a binary agrobacterium vector or a direct DNA delivery vector.

7. A plant cell transformed with a vector as claimed in claim 5.

8. A genetically transformed plant or part thereof having stably incorporated into the genome the DNA construct as claimed in claim 3 or claim 4.

9. A plant cell or genetically transformed plant according to claim 7 or claim 8, wherein the plant is wheat, maize, oil seed rape, potato, tomato, banana or tobacco.

10. A method of increasing the resistance of a plant to infection by a pathogenic organism, the method comprising transforming the plant with a vector comprising a promoter according to claim 1 or claim 2 operably linked to a gene conferring resistance to the pathogenic organism.

11. A method as claimed in claim 10 wherein the pathogenic organism is a fungus and the gene encodes an antifungal protein.

12. A genetically transformed plant or part thereof according to claim 8 which is a cell, protoplast or seed.

* * * * *